(12) United States Patent
Kurz et al.

(10) Patent No.: US 11,796,540 B2
(45) Date of Patent: Oct. 24, 2023

(54) METHODS FOR MODULATING SIGNAL INTENSITY IN INTERACTION ASSAYS

(71) Applicant: Roche Diagnotics Operations, Inc., Indianapolis, IN (US)

(72) Inventors: Georg Kurz, Penzberg (DE); Eloisa Lopez-Calle, Ludwigshafen (DE); Ewelina Hegel, Mannheim (DE); Josef Roedl, Mutterstadt (DE); Eva Hoess, Neuried (DE); Joerg Kaufmann, Iffeldorf (DE); Marisa Kirchenbauer, Dossenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/522,743

(22) Filed: Jul. 26, 2019

(65) Prior Publication Data

US 2019/0346439 A1    Nov. 14, 2019

Related U.S. Application Data

(63) Continuation of application No. PCT/EP2018/051962, filed on Jan. 26, 2018.

(30) Foreign Application Priority Data

Jan. 27, 2017    (EP) ..................... 17153514

(51) Int. Cl.
*G01N 33/543*    (2006.01)
*C08F 220/06*    (2006.01)
*G01N 33/68*    (2006.01)
*C08F 220/58*    (2006.01)

(52) U.S. Cl.
CPC ..... *G01N 33/54393* (2013.01); *C08F 220/06* (2013.01); *C08F 220/585* (2020.02); *G01N 33/6863* (2013.01); *G01N 2333/4737* (2013.01)

(58) Field of Classification Search
CPC ......... G01N 33/54393; G01N 33/6863; G01N 2333/4737; C08F 212/14; C08F 220/06; C08F 220/58; C08F 220/585; C08F 212/30
See application file for complete search history.

(56) References Cited

U.S. PATENT DOCUMENTS

| 4,319,882 | A | 3/1982 | Sharma |
| 4,362,531 | A | 12/1982 | de Steenwinkel et al. |
| 7,279,339 | B2 | 10/2007 | Sumida et al. |
| 7,368,252 | B2 | 5/2008 | Sumida et al. |
| 10,119,963 | B2 | 11/2018 | Takahashi et al. |
| 2001/0026927 | A1 | 10/2001 | Yokohama et al. |
| 2009/0061455 | A1 | 3/2009 | Sankaran et al. |
| 2010/0167310 | A1 | 7/2010 | Yamamoto et al. |
| 2012/0094394 | A1 | 4/2012 | Burkhard |

FOREIGN PATENT DOCUMENTS

| CN | 101377488 A | 3/2009 |
| DE | 102006000707 A1 | 7/2007 |
| EP | 0332021 A2 | 9/1989 |
| EP | 0503454 A1 | 9/1992 |
| EP | 0667529 A2 | 8/1995 |
| EP | 0713095 A2 | 5/1996 |
| EP | 0786666 A1 | 7/1997 |
| EP | 1130396 A1 | 9/2001 |
| EP | 1321770 A2 | 6/2003 |
| EP | 1355154 A2 | 10/2003 |
| EP | 1610128 A1 | 12/2005 |
| EP | 1956373 A1 | 8/2008 |
| EP | 1970704 A1 | 9/2008 |
| EP | 2698633 A1 | 2/2014 |

(Continued)

OTHER PUBLICATIONS

Min Qui ("Poly (4-styrenesulfonic acid-co-maleic acid) is an entry inhibitor against both HIV-1 and HSV infections—Potential as a dual functional microbicide", Antiviral Research, vol. 96, pp. 138-147, published 2012) (Year: 2012).*
Tamiyakul ("Changes in protein patterns of *Staphylococcus aureus* and *Escherichia coli* by silver nanoparticles capped with poly (4-styrenesulfonic acid-co-maleic acid) polymer", Asian Biomed (Res Rev News), vol. 13, pp. 39-47, published 2019) (Year: 2019).*
Anonymous, TechNote 301 Immunological Application, Bangs Laboratories, Inc., 2013, 13 pp., Rev. #003, Active.

(Continued)

*Primary Examiner* — Shafiqul Haq
*Assistant Examiner* — Nam P Nguyen
(74) *Attorney, Agent, or Firm* — Stinson LLP

(57) ABSTRACT

The disclosure includes a method for determining an analyte in a sample in an interaction assay, including contacting a sample with an interaction modulator, wherein the interaction modulator is Poly-(4-styrenesulfonic acid-co-maleic acid) (PSSM), aminodextran, carboxymethyldextran, Poly-(2-acrylamido-2-methyl-1-propanesulfonic acid (PAMPS), triethylamine, triethanolamine, taurine, or dodecylsulfate. The disclosure includes a method for determining an analyte in an interaction assay, including contacting the sample with an interaction modulator, wherein the interaction modulator is an enhancer of the interaction assay at low analyte concentrations and is a retarder of the interaction assay at high analyte concentrations and wherein the interaction modulator is Poly-(4-styrenesulfonic acid-co-maleic acid) (PSSM) and/or Polyacrylic acid (PAA). The disclosure further relates to a kit having a detection agent specifically detecting an analyte and at least one interaction modulator. Further, the present disclosure relates to devices relating to the methods and kits.

10 Claims, 15 Drawing Sheets

(56) References Cited

FOREIGN PATENT DOCUMENTS

| EP | 2720041 A1 | 4/2014 |
|---|---|---|
| JP | 2007155623 A | 6/2007 |
| WO | 1994/023297 A1 | 10/1994 |
| WO | 1996/0023839 A1 | 2/1996 |
| WO | 1996/012966 A1 | 5/1996 |
| WO | 2005/083433 A1 | 9/2005 |
| WO | 2007/076013 A1 | 7/2007 |
| WO | 2010/118861 A1 | 10/2010 |
| WO | 2012133482 A1 | 10/2012 |

OTHER PUBLICATIONS

Feng, Da-Fei and Doolittle, Russell F., Progressive Sequence Alignment as a Prerequisite to Correct Phylogenetic Trees, Journal of Molecular Evolution, 1987, pp. 351-360, vol. 25.

Fujimoto, Tetsuya et al., Development of a Latex Immunoturbidimetric Assay for the Automated Measurement of α2 Plasmin Inhibitor-Plasmin Complex in Human Plasma, Seminars in Thrombosis and Hemostasis, 1999, pp. 551-556, vol. 25, No. 6.

Gribnau, T.C.J. et al., Particle-Labelled Immunoassays: A Review, Journal of Chromatography Biomedical Applications, 1986, pp. 175-189, vol. 376.

Higgins, D. G. and Sharp, P. M., Fast and sensitive multiple sequence alignments on a microcomputer, Computer Applications in the Biosciences: CABIOS, 1989, pp. 151-153, vol. 5, Abstract only.

Holownia, Peter et al., Effect of Poly(ethylene glycol), Tetramethylammonium Hydroxide, and Other Surfactants on Enhancing Performance in a Latex Particle Immunoassay of C-Reactive Protein, Analytical Chemistry, 2001, pp. 3426-3431, vol. 73.

International Search Report dated Oct. 16, 2018, in Application No. PCT/EP2018/051962, 3 pps.

Molina-Bolívar, J. A. et al., Agglutination kinetics of F(ab')2 coated polymer colloids, Colloid & Polymer Science, 1998, pp. 1117-1124, vol. 276.

Needleman, Saul B. and Wunsch, Christian D., A General Method Applicable to the Search for Similarities in the Amino Acid Sequence of Two Proteins, Journal of Molecular Biology, 1970, pp. 443-453, vol. 48.

Newman, D. J. et al., Particle enhanced light scattering immunoassay, Annals of Clinical Biochemistry, 1992, pp. 22-42, vol. 29.

Price, C. P. et al., Light-scattering immunoassay of specific proteins: a review, Annals of Clinical Biochemistry: International Journal of Laboratory Medicine, 1983, pp. 1-14, vol. 20.

Reverberi, Roberto and Reverberi, Lorenzo, Factors affecting the antigen-antibody reaction, Blood Transfusion, 2007, pp. 227-240, vol. 5.

Sharma, Vivek et al., Rheology of globular proteins: apparent yield stress, high shear rate viscosity and interfacial viscoelasticity of bovine serum albumin solutions, Soft Matter, 2011, pp. 5150-5160, vol. 7.

Smith, Temple F. and Waterman, Michael S., Comparison of Biosequences, Advances in Applied Mathematics, 1981, pp. 482-489, vol. 2.

\* cited by examiner

METHODS FOR MODULATING SIGNAL INTENSITY IN INTERACTION ASSAYS

CROSS-REFERENCE TO RELATED APPLICATIONS

This application is a continuation of International Application No. PCT/EP2018/051962 filed Jan. 26, 2018, which claims priority to European Application No. 17153514.9 filed Jan. 27, 2017, the closures of which are hereby incorporated by reference in their entirety.

SUMMARY

The present invention relates to a method for determining an analyte in a sample in an interaction assay, said method comprising contacting said sample with an interaction modulator, wherein said interaction modulator is selected from the list consisting of Poly-(4-styrenesulfonic acid-co-maleic acid) (PSSM), aminodextran, carboxymethyldextran, Poly-(2-acrylamido-2-methyl-1-propanesulfonic acid (PAMPS), triethylamine, triethanolamine, taurine, and dodecylsulfate. The present invention also relates to a method for determining an analyte in a sample in an interaction assay, said method comprising contacting said sample with an interaction modulator, wherein said interaction modulator is an enhancer of said interaction assay at low analyte concentrations and is a retarder of said interaction assay at high analyte concentrations and wherein said interaction modulator is Poly-(4-styrenesulfonic acid-co-maleic acid) (PSSM) and/or Polyacrylic acid (PAA). The present invention further relates to a kit comprising a detection agent specifically detecting an analyte in a sample and at least one interaction modulator of the present invention. Further, the present invention relates to devices and uses relating to the methods and kits of the present invention.

BACKGROUND

Immunoassays, in particular homogenous immunoassays, are versatile test systems for the automated conduction of in vitro diagnostic tests, since they provide means for a fast, cost-effective and accurate determination of analytes in clinical samples. Homogeneous immunoassays have the benefits of being quasihomogeneous assays which do not require any separation or wash step for removing the unbound binding partner(s) from the bound complex. Due to their easy one-step procedure and their short turnaround times homogeneous immunoassays are ideal candidates for the application in automated analyzers and are routinely used in the clinical diagnostics for the quantitation of serum proteins, therapeutic drugs and drugs of abuse on clinical chemistry analyzers. A particular class of homogeneous immunoassays are the agglutination immunoassays in which a specific antigen or antibody is detected based on the specific agglutination reaction between the antigen and the antibody. In such immunoassays usually the binding partners, an antibody against an antigen that is to be determined or an antigen against an antibody that is to be determined, and the sample that may contain the analyte to be determined are brought into contact, and the magnitude of the agglutination resulting from the complex formation of the binding partners is determined by turbidimetric or nephelometric measurements of the sample. The optical signals of these measurements correlate with the amount of analyte.

Specific compounds are known to modulate (accelerate or decelerate) the reaction kinetic of agglutination immunoassays, leading to a modulation (increase or decrease) of signal intensity. For low analyte concentrations, higher signal intensity is required to obtain sufficient analytical sensitivity and reportable results in the low-concentration range of the measuring range of an assay. For high analyte concentrations, lower signal intensity is required to obtain distinguishable optical signals and reportable results in the high-concentration range of the measuring range. Methods for the modulation of the signal intensity have the potential to broaden the measuring range of the assays, either at the lower end or the upper end, or at both. Such methods also allow a fast and improved test development by the systematic use of the modulating compounds for establishing the required analytical sensitivity and dynamic range. Current immunoassays often do not cover the entire analyte concentration range present in clinical samples with state-of-the-art methods.

US 2012 0094 394 describes the retarding effect of chaotropic reagents on agglutination assays. The inventor addresses the problem, that measurement of analytes is only possible in a certain concentration range, which is called the dynamic range. Excess analyte concentrations fail to generate an agglutination reaction. In order to measure sample concentrations, which exceed the measurable concentration range, dilution steps have to be performed. These dilution steps increase the work load as well as the assay time and the assay costs. According to the invention, the increase of the dynamic range for the determination of higher concentrations in turbidimetric immunoassays was successfully achieved by the addition of chaotropic reagents like Urea. This compound leads to lower signal intensities and distinguishable signals at the higher concentration range of the dose-response curve thus yielding a higher upper measuring range. Yet, the proposed mechanism is also the drawback of the chaotropic compounds: Chaotropic compounds disrupt the 3-D structure of antibodies and upon that change the affinity of the antibody to the antigen. Therefore, higher analyte concentrations can generate distinguishable, concentration correlated signals. But, depending on the antibody utilized and the analyte of interest, this mechanism can adversely affect the assay performance. Even the destruction of the detected epitope can happen. In U.S. Pat. No. 4,362,531 chaotropic reagents are used as additives for reducing non-specific binding in the assay.

Further, the following modulators have been described: Polyethyleneglycol (PEG) is generally known as reaction accelerator of agglutination reactions, leading to a faster increase of the turbidimetric signal in immunoassays (cf. e.g. C P Price, K Spencer and J Whicher, Ann. Clin. Biochem. 1983, 20, 1). However, depending on the molecular weight of the PEG, its addition may dramatically increase the viscosity of the reaction mixture leading to reduced diffusion and errors in automatic pipettors (Peter Holownia, Soledad Perez-Amodio, and Christopher P. Price, Anal. Chem. 2001, 73, 3426). Other hydrophilic polymers, such as polyvinylpyrrolidone (PVP, cf. e.g. EP 0 503 454), polyvinylacetate (PVA, cf. e.g. DE 1020 06000707), dextran (cf. e.g. WO 96/12966), alginates (EP 1 355 154), Polybrene and Protamine (Roberto Reverberi, Lorenzo Reverberi, Blood Transfusion 2007, 5, 227), zwitterionic acrylate-based polymers (U.S. Pat. No. 7,368,252; EP 2 720 041) behave similar to PEGs. The hydrophilic anionic polymers polyacrylic acid (PAA) and polymethacrylic acid (PMMA) are reported to act as compounds improving the performance of competitive homogeneous agglutination immunoassays for aminoglycoside antibiotics by expanding the upper detection range (EP 0 786 666). The dextran-derivate dextransulfate and PAA (WO 2007 076013) were found to reduce interferences in homocysteine immunoassays caused by blood sample components.

Also the application of NaCl as reagent for increasing the ion strength of the assay have been reported to reduce reaction kinetic and signal intensities of immunoassays (J. A. Molina-Bolôvar et al, Colloid Polym. Sci. 1998, 276, 1117). Therefore, NaCl can be used as a retarder. Salt addition however may lead to non-optimal conditions and analytical sensitivity of an immunoassay especially when the concentration is outside of the optimal ion strength for the antigen-antibody reaction.

Members of the group of amines were described as accelerators of homogeneous immunoassays (US 2010/0167 310). The amines acting as modulators are benzylamine, 2-amino-2-thiazoline and benzamidine, which were proposed to be applicable for turbidimetric immunoassays such as the Albumin assay. Other publications describe amines as suppressors of non-specific binding in immunoassays (EP 0 667 529; EP 1 321 770). Amine oxides as another group of amine derivates, described in EP 0332021, are used to improve the sensitivity of immunoassays. Amino acids like 6-aminohexanoid acid reduce the non-specific binding in particle-enhanced turbidimetric immunoreactions (Seminars in Thrombosis and Hemostasis 1999, 25, 551) and arginine also reduces the phenotype variability of antigens in latex-enhanced immunoassays (EP1610128).

The compound class of surfactants was described as accelerators of turbidimetric immunoassays ryvo 96 04555), accelerators of hem-agglutination reactions (U.S. Pat. No. 4,319,882) and signal enhancer in chemiluminescence based assays (WO 96/02839). WO 94 23297 addresses the improvement of immunoassays by the addition of anionic surfactants such as SDS which strongly reduce the non-specific binding reactions in the assay. Similar behavior of surfactants as non-specific binding suppressor is published in WO 2005/083433 and EP 0 713 095 for non-ionic detergents.

A method for the determination of the C-reactive protein using phosphocholine derivatives in a particle-enhanced turbidimetric immunoassay is described in US 2001/0026927. The application of such compounds retards the agglutination reaction in said assay. The achieved signal decrease allows the measurement of higher analyte concentrations.

There is, thus, a need in the art for improved means and methods for modulating assays involving interaction of two binding partners, avoiding the drawbacks of the prior art. This problem is solved by the means and methods disclosed herein.

DETAILED DESCRIPTION

Figure 1A:
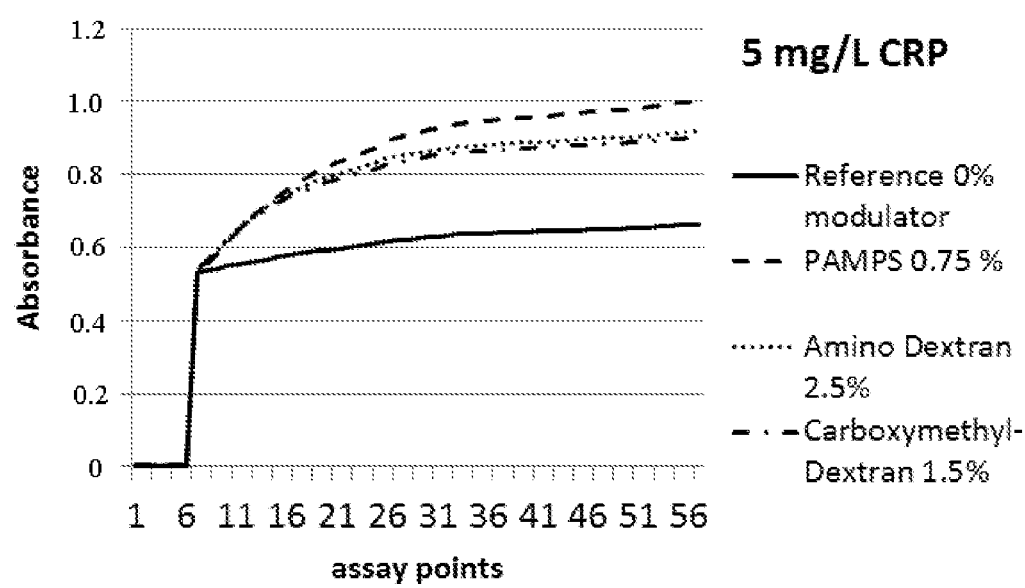
FIG. 1A: Modulator compounds as CRP-assay enhancers: change of absorbance of a homogenous CRP assay over time in a control assay or in the presence of 5 mg/L CRP as modulator.

Accordingly, the present invention relates to a method for determining an analyte in a sample in an interaction assay, said method comprising contacting said sample with an interaction modulator,
wherein said interaction modulator is selected from the list consisting of Poly-(4-styrenesulfonic acid-co-maleic acid) (PSSM), aminodextran, carboxymethyldextran, Poly-(2-acrylamido-2-methyl-1-propanesulfonic acid (PAMPS), triethylamine, triethanolamine, taurine, and dodecylsulfate.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

Moreover, if not otherwise indicated, the term "about" relates to the indicated value with the commonly accepted technical precision in the relevant field, preferably relates to the indicated value ±20%, more preferably ±10%, most preferably ±5%. The term "water", as used herein, relates to deionized water, in an embodiment double deionized or double distilled water. Furthermore, a term relating to an acid or a base, if not otherwise indicated, includes the salts of this compound, in an embodiment includes physiological salts of the compounds. In particular, included are alkali metal and earth alkali metal salts of acids, in particular Li, Na, K, Ca, and Mg salts; and in particular included are halogenide, in particular chloride, sulfate, nitrate, and tosylate salts of bases. Thus, a cation, in an embodiment, is an alkali metal or an earth alkali metal cation, in particular $Li^+$, $Na^+$, $K^+$, $Ca^{2+}$, or $Mg^{2+}$, in an embodiment is $Na^+$.

The method of the present invention, preferably, is an in vitro method. Thus, in an embodiment, the method is not performed on the body of a living subject. In an embodiment, the method is performed on an isolated sample. Moreover, the method may comprise steps in addition to those explicitly mentioned above. For example, further steps may relate, e.g., to obtaining a sample, or to providing a value determined to a user. Moreover, one or more of said steps may be performed by automated equipment. In an embodiment, the method provides information aiding to the medical practitioner in establishing a diagnosis.

As used herein, the term "determining" refers to determining at least one feature, in an embodiment immunological feature, of an analyte to be determined by the method of the present invention in a sample. Features in accordance with the present invention, in an embodiment, are structural features of the analyte facilitating detection of the analyte, in an embodiment by immunological means. Accordingly, typical features are features facilitating differentiation of said analyte from other chemical compounds in a sample. In an embodiment, determining an analyte is establishing whether an analyte is present or absent in the sample at a concentration above the detection limit of the method. Methods of determining a detection limit are known to the skilled person. In a further embodiment, determining is determining semi-quantitatively or quantitatively the amount or concentration of an analyte in a sample. For quantitative determination, either the absolute or precise amount of the analyte will be determined or the relative amount of the analyte will be determined. The relative amount may be determined in a case were the precise amount of an analyte can or shall not be determined. In such case, it may be determined whether the amount in which the analyte is present is increased or diminished with respect to a second sample comprising said analyte in a second amount. In an embodiment, said feature facilitates identification, in a further embodiment, quantification of the analyte by immunological means.

The term "interaction assay", as used herein, relates to an assay in which determination of the analyte is based on the interaction of the analyte with a detection agent. In an embodiment, said interaction is a specific interaction, i.e., in an embodiment, is an interaction in which the affinity between the detection agent and the analyte is at least 10 fold, in a further embodiment at least 100 fold, in a further embodiment at least 1000 fold higher compared to the affinity between the detection agent and a further compound present in the sample. As will be further understood by the skilled person, the determination of analyte/detection agent complexes will depend on the assay format chosen.

In an embodiment, the interaction assay is a non-homogenous interaction assay, i.e. is an interaction assay comprising separation of analyte/detection agent complexes from the sample. Non-homogenous interaction assays are well known in the art and include interaction assays in which the analyte is bound to a solid surface, in particular to the surface of an assay plate or of a bead; as is understood by the skilled person, said binding to a solid surface may be direct or indirect, e.g. via an antibody as, e.g. in an enzyme-linked immunoassay (ELISA).

In an embodiment, the interaction assay is a homogenous assay, in an embodiment a homogenous immunoassay in a further embodiment a homogenous agglutination immunoassay. Thus, in an embodiment, the assay is an assay in which the analyte, the detection agent and analyte/detection agent complexes potentially present are not separated from the assay mixture for detection. Thus, in an embodiment, the presence of analyte/detection agent complexes is detected by determining a change in a physical and/or chemical property of the detection mixture, in an embodiment an optical property as specified herein below. In an embodiment, the homogenous assay, in particular the homogenous agglutination immunoassay, is an assay for c-reactive protein (CRP); for albumin; for one or more serum proteins, in an embodiment ferritin, myoglobin, D-dimer, rheumatoid factors, HbA1c, Antistreptolysin O, Cystatin C, Soluble Transferrin Receptor, lipoprotein (a), and/or β2-Microglobulin; for therapeutic drugs, in an embodiment digitoxin, digoxin, phenobarbital, cyclosporine A, amikacin, carbamazepine; and/or for drugs-of-abuse, in an embodiment a barbiturate, an amphetamine, and/or cocaine. In an embodiment, the interaction assay is an agglutination assay, in an embodiment is an agglutination immunoassay. In a further embodiment, the interaction assay is a bead-enhanced agglutination assay, in a further embodiment is a latex-enhanced agglutination assay, in a further embodiment is a bead-enhanced agglutination immunoassay, in a further embodiment is a latex-enhanced agglutination immunoassay, e.g. a CRP assay. In an embodiment, the interaction assay is a non-latex-enhanced agglutination assay, in a further embodiment is a non-bead-enhanced agglutination assay, in a further embodiment is a non-latex-enhanced agglutination immunoassay, in a further embodiment is a non-bead-enhanced agglutination immunoassay, e.g. an albumin assay. The different assay formats such as bead-enhanced assay, bead-enhanced agglutination assay, latex-enhanced agglutination assay, latex-enhanced agglutination immunoassay and their non-bead enhanced counterparts are known to the skilled person (cf. e.g. Bangs TechNote 301 (1999), Bangs Laboratories, Inc.; CP Price (2001), Encyclopedia of Life Sciences, John Wiley & Sons, Ltd.: 1-7, DOI: 10.1038/npg.els.0001114; Gribnau et al. (1986), J Chromatography 376:175, The immunoassay handbook (4th ed. 2013), Ed. David Wild: homogeneous immunoassays, E. F. Ullmann).

In an embodiment, the method comprises determining a first value of an interaction-related parameter before addition of a starter compound, and determining a at least one second value of an interaction-related parameter after addition of said starter compound.

The term "interaction-related parameter", as used herein, relates to a parameter correlating with the degree of interaction between at least the analyte and the detection agent in the detection reaction and, thus, in an embodiment, correlates with the amount of analyte present in the detection reaction. Thus, the interaction parameter may, in principle, be any measurable parameter showing the aforesaid correlation. E.g. in an embodiment, the interaction-related parameter may be a mass or the size of a precipitate formed, a viscosity, or the like. In an embodiment, the interaction-related parameter is a transmission-related parameter as specified herein below. It is known to the skilled person that the aforesaid interaction-related parameter may be used to determine an analyte, e.g. by determining the value of said interaction-related parameter at a given point in time after starting the detection reaction, by determining when a plateau in the graphical representation of values over time is reached, by determining the value of the interaction-related parameter after said plateau is reached and/or from the slope of a graph representing the change of the values of said interaction-related parameter over time. Accordingly, in an embodiment, in the method according to the present invention, a multitude of values of said interaction-related parameter of the same sample is determined at time intervals, in an embodiment at regular time intervals. In an embodiment, a value of said interaction-related parameter is measured in a sample at least every 10 s, in a further embodiment at least every 8 s, in a further embodiment at least every 5 s, in a further embodiment at least every 3 s, in a further embodiment at least every 2 s, in a further embodiment at least every second, in a further embodiment at least every 0.2 s. In a further embodiment, a value of said interaction-related parameter is measured in a sample continuously. As is understood by the skilled person, determining an interaction-related parameter, in an embodiment, comprises at least establishing a signal correlating with the interaction-related parameter and actual recording values of said signal. While a signal correlating with the interaction-related parameter may be provided truly continuously e.g. as a voltage measured in a photocell of a photometer, or may be provided in discrete measurements, e.g. by moving a well of a multi-well plate into the light path of a photometer, recording of values of said signal will be in discrete steps at given points in time. Nonetheless, as used herein, the term "continuously determining values of a interaction-related parameter" relates to determining values of a interaction-related parameter more frequent than every 0.2 s, e.g. at least every 0.1 s. Thus, the term relates to recording values of the interaction-related parameter at the aforesaid frequency.

As indicated above, in an embodiment, the interaction-related parameter may also be determined at least once, in a further embodiment exactly once, at a predetermined point in time after the detection reaction was started. In an embodiment, the interaction-related parameter, in such case, is determined additionally before the detection reaction was started or immediately thereafter, and the value of the interaction-related parameter thus obtained is, in an embodiment, subtracted from the value of the interaction-related parameter determined at a time point later after the detection reaction was started. As is understood by the skilled person, a detection reaction is started at the point in time the analyte is contacted with the detection agent. Thus, as used herein, the term "starter compound" relates to the analyte or to the detection agent, whichever is added to the detection mixture later.

In an embodiment, the interaction assay is a photo-optical assay, i.e. determining the analyte comprises determining at least one transmission-related parameter in said sample. Thus, the interaction-related parameter, in such embodiment, is a transmission-related parameter. The term "transmission-related parameter", as used herein, relates to a parameter indicating or correlating with the ratio of transmitted light versus incident light of a sample or to a parameter derived therefrom. In an embodiment, a transmission-related parameter is derived from the aforesaid ratio by standard operations of mathematics, physics and/or chemistry. Accordingly, in an embodiment, the transmission-related parameter is a transmission coefficient, an extinction coefficient, a transmittance, an absorbance, or an absorption. Moreover, in an embodiment, the transmission-related parameter is a value derived from one of the aforesaid parameters by a standard mathematical operation, e.g. to correct for a dilution applied to a sample, for a calibration factor, or the like. Methods for determining a transmission-related parameter in a sample are known to the skilled person and include, in an embodiment, transmission measurement, nephelometry, or turbidimetry. Such methods are, in an embodiment, implemented in sample analyzers known in the art. In an embodiment, a transmission-related parameter is determined by turbidimetry; thus, in an embodiment, the interaction is a turbidimetric or a nephelometric assay. A transmission-related parameter may be determined at one or more specific wavelength(s); thus, in an embodiment, a transmission-related parameter is determined at a wavelength of from 350 nm to 700 nm, in an embodiment of from 300 nm to 700 nm, in an embodiment of from 300 nm to 600 nm and/or of from 500 nm to 700 nm.

The term "analyte", as used herein, relates to a chemical molecule, in an embodiment, an organic molecule, binding to a detection agent of the present invention with sufficient affinity to allow detection of an analyte/detection agent complex. In an embodiment, the dissociation constant ($K_d$) of the analyte/detection agent complex is at most $10^{-7}$ mol/L, in a further embodiment, at most $10^{-8}$ mol/l, in a further embodiment, at most $10^{-9}$ mol/L, in a further embodiment, at most $10^{-19}$ mol/L, in a further embodiment, at most $10^{-11}$ mol/L, in a further embodiment, at most $10^{-12}$ mol/L. Thus, in an embodiment, the term "analyte" includes any substance for which there exists a specific reaction partner (e.g., a binding molecule or substance which specifically binds the analyte), or for which a specific binding partner can be prepared. An analyte that can be determined by an interaction assay of the invention may, in an embodiment, be an antigenic analyte, the binding partner then suitably being an immunological binding partner, in particular an antibody. The antigenic analyte may be monomeric or polymeric, with or without repetitive epitopes. In an embodiment, the analyte is a naturally occurring analyte. In a further embodiment, the analyte is a non-naturally occurring analyte, in an embodiment is an artificial analyte. In an embodiment, the analyte is any in vitro diagnostic compound such as e.g. a serum protein, a therapeutic drug or a drug of abuse, as specified elsewhere herein. Representative analytes include, but are not limited to antigens, haptens, antibodies, proteins, peptides, amino acids, hormones, steroids, cancer cell markers, tissue cells, viruses, vitamins, nucleic acids, and pesticides. In an embodiment, an analyte The term "analyte" includes any substance for which there exists a specific reaction partner (e.g., a binding molecule or substance which specifically binds the analyte), or for which a specific binding partner can be prepared. Analytes that can be determined by the assay of the invention include antigenic analyte, the binding partner then suitably being immunological binding partners. The antigenic analytes may be monomeric or polymeric, with or without repetitive epitopes. In an embodiment, the analyte is the substance whose presence and/or concentration in a sample is to be determined.

In an embodiment, the analyte has a molecular mass of at least 100 (corresponding to 100 atomic mass units, and to 100 Da; 1 Da corresponding to $1.66 \times 10^{-27}$ kg), in a further embodiment, at least 250, in a further embodiment, at least 500, or, in a further embodiment, at least 1000. In an embodiment, the analyte is a biological molecule, in a further embodiment, the analyte is a biological macromolecule. In a further embodiment, the analyte is a polypeptide, in an embodiment is an antigen, in particular a polypeptide, or an antibody produced against said antigen. In an embodiment, the analyte is an antigen produced by an infectious agent, e.g., a virus or bacterium, or is an antibody produced by a subject against an antigen produced by an infectious agent. In an embodiment, the infectious agent is a prion, a virus, a bacterium, or an eukaryotic pathogen, e.g. a fungus, an amoeba, or a plasmodium. In a further embodiment, the infectious agent is human-pathogenic prion, a human-pathogenic virus, a human-pathogenic bacterium, or a human-pathogenic eukaryotic pathogen. In a further embodiment, the analyte is an antigen produced by the body of a subject or by a fetus it carries, or is an antibody against an antigen produced by the body of a subject or by a fetus it carries; thus, in an embodiment, the analyte is an autoantibody.

The term polypeptide, as used herein, in an embodiment, includes variants and fragments of the specifically indicated polypeptides. Variants include polypeptides comprising amino acid sequences which are at least 70%, at least 75%, at least 80%, at least 85%, at least 90%, at least 95%, at least 98% or at least 99% identical to the amino acid sequences specifically indicated. The percent identity values are, preferably, calculated over the entire amino acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. A polypeptide comprising a fragment of any of the polypeptides specifically referred to, in an embodiment, is also encompassed as a polypeptide of the present invention, as long as said fragment still comprises the epitope which is detected by the detection agent. Accordingly, the polypeptide may comprise or consist of the domains of the polypeptide of the present invention conferring the said biological activity. A fragment as meant herein, preferably, comprises at least 10, in an embodiment at least 200, in a further embodiment at least 50, in a further embodiment at least 100 consecutive amino acid residues corresponding an amino acid sequence of any one of the polypeptides specifically referred to.

In an embodiment, the analyte is a small molecule antigen, i.e. the analyte has a molecular mass of at most 1000. In an embodiment, the analyte is a therapeutic drug or a drug of abuse, as specified elsewhere herein.

The term "detection agent", as used herein, relates to a chemical molecule binding, directly or indirectly, to the analyte of the present invention as specified herein above. In an embodiment, the detection agent is not bound to a solid surface and not adapted to be bound to a solid surface. As will be understood by the skilled person, the detection agent may also be an indirect detector compound, i.e. a detection agent not contacting the analyte directly, but by means of a further compound which itself binds to the analyte. In an embodiment, the detection agent is a direct detection agent, i.e. is an agent directly binding to the analyte. As will be understood by the skilled person, the designations "analyte" and "detecting agent", in particular in homogenous assays, are designations merely attributed in view of which compound is to be detected and which compound is added to a sample in order to detect the analyte; thus, the analyte in a first assay may be the detection agent in a second assay, and vice versa. Accordingly, the definitions provided above for the analyte of the present invention apply to the detection agent of the present invention mutatis mutandis. In an embodiment, the detection agent is an antibody, in an embodiment is an IgG. In an embodiment, the detection agent is a monoclonal antibody. In a further embodiment, the detection agent is an antibody, in an embodiment a monoclonal antibody bound to a latex bead. In an embodiment, the detection agent is a an agent comprising at least two diagnostic epitopes, i.e. epitopes binding to an analyte. In a further embodiment, said diagnostic epitopes are identical, such as, e.g. in an IgG.

The term "sample", as used herein, refers to any composition of matter suspected or known to comprise at least one analyte. In an embodiment, the sample is a sample of a subject, in an embodiment of a patient; in an embodiment, the sample is an isolated sample from a subject. Thus, in an embodiment, a sample is a sample of a body fluid, in an embodiment, blood, plasma, serum, saliva or urine, or a sample derived by lavage from tissues or organs, e.g. from the respiratory tract. In a further embodiment, the sample is a blood, plasma, serum or urine sample. In a further embodiment, the sample is a blood or plasma sample or is a serum or plasma sample, in a further embodiment is a plasma sample. In an embodiment, in case the sample is a blood sample, the method of the present invention comprises a further step of obtaining a serum or plasma sample from said blood sample, or comprises hemolysing said sample. In an embodiment, the sample is a citrate plasma sample, a heparin plasma sample, or an EDTA plasma sample. Biological samples can be derived from a subject as specified elsewhere herein. Techniques for obtaining the aforementioned different types of biological samples are well known in the art. For example, blood samples may be obtained by blood taking, e.g. by puncturing an arterial and/or a venous blood vessel. In an embodiment, the sample is a fasting sample, in particular a fasting blood, plasma or serum sample. In an embodiment, the sample is a sample of cells, tissue, or an organ obtained from a subject. In an embodiment, in case said organ is live-critical, said subject is not a human. Such samples can be obtained by well-known techniques including, in an embodiment, scrapes, swabs or biopsies appropriate regions of a body. As is known to the skilled person, such samples can be obtained by use of brushes, (cotton) swabs, spatulae, rinse/wash fluids, punch biopsy devices, puncture of cavities with needles or surgical instrumentation.

The aforementioned samples are, in an embodiment, pre-treated before they are used for the method of the present invention. Said pre-treatment may include treatments required to release or separate the compounds comprised in the sample or to remove excessive material or waste. Suitable techniques comprise centrifugation, extraction, fractioning, ultrafiltration, protein precipitation followed by filtration and purification and/or enrichment of compounds. As indicated herein above, pre-treatment may, e.g. be providing a plasma sample from a whole blood sample, providing a serum sample from a whole blood sample, or providing a serum sample from a plasma sample. Moreover, other pre-treatments are carried out in order to provide the compounds in a form or concentration suitable for analysis. Pre-treated samples as described before are also comprised by the term "sample" as used in accordance with the present invention.

The term "subject", as used herein, relates to an animal, in an embodiment a mammal, in a further embodiment a primate, in a further embodiment a human. In an embodiment, the subject is an experimental animal, in particular a mouse, rat, guinea pig, pig, or dog. In a further embodiment, the subject is a livestock or companion animal, in particular a cat, dog, goat, sheep, cattle, horse, or pig.

The term "contacting" as used in the context of the present invention is understood by the skilled person. In an embodiment, the term relates at least to bringing a sample and/or an analyte of the present invention into physical contact with a detection agent and an interaction modulator and thereby allowing the sample and/or analyte to interact with the detection agent and the interaction modulator. Thus, in an embodiment, contacting a sample and/or an analyte with an interaction modulator is including said interaction modulator in the detection reaction mixture.

The term "interaction modulator", as used herein, relates to a compound modifying the interaction between an analyte and a detection agent in an interaction assay as specified herein above. Said modification may relate to the velocity (kinetic) of the interaction, may relate to the extent of the interaction, or to both the velocity and the extent of interaction. As used herein, the "extent of interaction" relates to the intensity of a signal obtained in an interaction assay; thus, according to the present invention, it is immaterial whether a modulation in equilibrium signal is caused by a change in reaction equilibrium or is caused by a signal intensification, or both, in all cases it is, in an embodiment, assumed that the extent of interaction was modulated. In an embodiment, the interaction modulator is an enhancer, i.e. is an agent intensifying interaction; thus, the interaction enhancer, in an embodiment, is an agent increasing reaction velocity, i.e. is an interaction accelerator; in a further embodiment, the interaction enhancer is an interaction intensifier, i.e. is an agent increasing the extent of interaction, i.e., in an embodiment, increases equilibrium signal. In a further embodiment, the interaction modulator is an inhibitor, i.e. is an agent decreasing intensity of interaction; thus, the interaction inhibitor, in an embodiment, is an agent decreasing reaction velocity, i.e. is an interaction retarder; in a further embodiment, the interaction inhibitor is an interaction reducer, i.e. is an agent decreasing the extent of interaction, i.e., in an embodiment, decreases equilibrium signal. As will be understood, a modulation enhancer may be an interaction accelerator, an interaction intensifier, or both. Similarly, a modulation inhibitor may be an interaction retarder, an interaction reducer, or both. In an embodiment, an interaction modulator may also be both an interaction enhancer and an interaction inhibitor; in a further embodiment, said interaction modulator being both an interaction enhancer and an interaction inhibitor is Poly-(4-styrenesulfonic acid-co-maleic acid) (PSSM) as specified herein below, or is Polyacrylic acid (PAA) as specified herein below.

In an embodiment, the interaction modulator in aqueous solution has a density similar to the density of water; thus, an aqueous solution of the interaction modulator, in an embodiment, is easily miscible with other aqueous solutions or suspensions, in particular samples and/or reaction mixtures. In an embodiment, a 5% (w/v) solution of the interaction modulator in water has a density at 20° C. of from 0.8 kg/l to 1.2 kg/l, in an embodiment of from 0.9 kg/l to 1.1 kg/l, in a further embodiment of from 1.0 kg/l to 1.1 kg/l, a further embodiment of 1.05±0.2 kg/l. In an embodiment, density is measured by the U-tube oscillation method known to the skilled person, in an embodiment is performed on an Anton Paar Density meter DMA 35, in an embodiment according to instructions provided by the manufacturer. In a further embodiment, the interaction modulator is soluble in water at a concentration of at least 5% (w/v) at a temperature of 4° C.; thus, in an embodiment, a 5% (w/v) solution of the interaction modulator in water does not precipitate at a temperature of 4° C. In an embodiment, solubility is determined by visual inspection for precipitation (turbidity) after storage at 4° C. for at least 12 hours. In a further embodiment, solubility is determined by determining absorbance (optical density) of the sample at 600 nm after storage at 4° C. for at least 12 hours with 1 cm layer thickness; in such case, a compound is considered soluble in case the absorbance measured is less than 0.25, in an embodiment less than 0.1. In a further embodiment, the interaction modulator has a low absorbance at a wavelength potentially interfering with determining the analyte. Thus, in an embodiment, a 5% (w/v) solution of said interaction modulator has a molar extinction coefficient of less than 1000 $M^{-1}$ $cm^{-1}$, in a further embodiment less than 100 $M^{-1}$ $cm^{-1}$ at any wavelength selected from a range of from 400 nm to 700 nm, in a further embodiment of from 340 nm to 800 nm. In a further embodiment, a 5% (w/v) solution of said interaction modulator has a molar extinction coefficient of less than 1000 $M^{-1}$ $cm^{-1}$, in a further embodiment less than 100 $M^{-1}$ cm-1 at at least one, in an embodiment at least two, in a further embodiment at least three, in a further embodiment at least four, in a further embodiment at least five, in a further embodiment all of wavelengths 340 nm, 376 nm, 415 nm, 450 nm, 480 nm, 505 nm, 546 nm, 570 nm, 600 nm, 660 nm, 700 nm and 800 nm. In a further embodiment, an aqueous solution of the interaction modulator has a low viscosity. Thus, in an embodiment, the viscosity of a 5% (w/v) solution of said interaction modulator is less than 15 mPas, in an embodiment is less than 10 mPas. In an embodiment, viscosity is determined according to the Viscometer-Rheometer-on-a-Chip (VROC®) method (Sharma et al. (2011), Soft Matters 7:5150) at 20° C. In a further embodiment, viscosity determination is performed on a RheoSense m-VROC™ (Collotec) device at 20° C., in an embodiment according to instructions provided by the manufacturer. In a further embodiment, an aqueous solution of the interaction modulator has a low surface tension. Thus, in an embodiment, the surface tension of a 5% (w/v) solution of said interaction modulator in water is less than 100 mN/m, in an embodiment is less than 75 mN/m. In an embodiment, surface tension is determined according to the hanging-drop method known to the skilled person. In a further embodiment, surface tension is determined on a KRÜSS Easydrop device, in an embodiment according to instructions provided by the manufacturer. In an embodiment, an aqueous solution of the interaction inhibitor has at least two of the aforesaid properties, e.g., in an embodiment, has a density similar to water and has a low absorbance; or has a density similar to water and has a low viscosity; has a density similar to water and a low surface tension; or has a density similar to water and does not precipitate at a low temperature as specified above. In a further embodiment, an aqueous solution of the interaction inhibitor has at least three of the aforesaid properties, e.g., in an embodiment, has a density similar to water, has a low absorbance, and has a low viscosity; or has a density similar to water, has a low viscosity, and has a low surface tension. In a further embodiment, an aqueous solution of the interaction inhibitor has at least four of the aforesaid properties, e.g., in an embodiment, has a density similar to water, has a low absorbance, has a low viscosity, and has a low surface tension; or has a density similar to water, does not precipitate at a low temperature, has a low viscosity; and has a low surface tension. In a further embodiment, an aqueous solution of the interaction inhibitor has all five of the aforesaid properties, i.e. has a density similar to water, does not precipitate at a low temperature, has a low absorbance, has a low viscosity, and has a low surface tension. In an embodiment, the interaction modulator is a compound as specified herein in the Examples and has the aforementioned properties as specified in the Examples.

In an embodiment, the interaction modulator is Poly-(4-styrenesulfonic acid-co-maleic acid) (PSSM); thus in an embodiment, the interaction modulator is a copolymer of 4-styrenesulfonic acid and maleic acid. In an embodiment, said PSSM has a repeating structural unit according to formula (I):

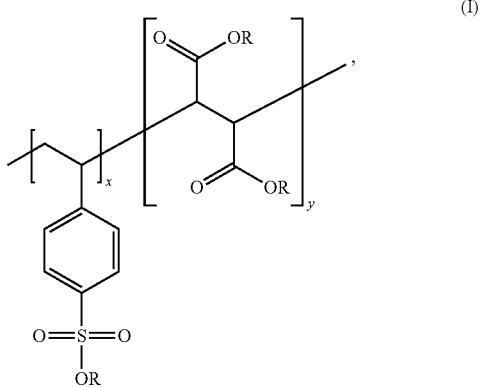

(I)

with x and y being integers selected from 0, 1, 2, 3, 4, and 5, said selection being independent for x and y and for each repeating unit; and R being H or a cation, in an embodiment an inorganic cation, in a further embodiment a cation as specified herein above. In a further embodiment, PSSM has a molecular weight of from 1 kDa to 100 kDa, in an embodiment of from 5 kDa to 50 kDa, in a further embodiment of about 20 kDa. In an embodiment, PSSM is a copolymerisate of a molar 1:1 mixture of 4-styrenesulfonic acid and maleic acid. In a further embodiment, the interaction modulator is the sodium salt of PSSM, in a further embodiment is the compound described by CAS number 68037-40-1 and/or MDL No. MFCD00217739.

In an embodiment, the interaction modulator is Poly-(2-acrylamido-2-methyl-1-propanesulfonic acid (PAMPS); thus, in an embodiment, the interaction modulator is a polymer of 2-acrylamido-2-methyl-1-propanesulfonic acid. In a further embodiment, PAMPS has a repeating structural unit according to formula (III):

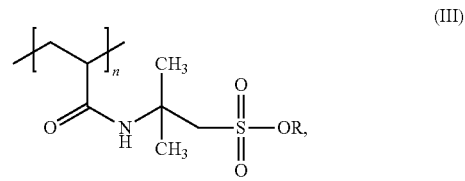

(III)

with R being H or a cation, in an embodiment an inorganic cation, in a further embodiment a cation as specified herein above. In a further embodiment, PAMPS has a molecular weight of from 100 kDa to 10000 kDa, in an embodiment of from 500 kDa to 5000 kDa, in a further embodiment of about 2000 kDa. In a further embodiment, the interaction modulator is the compound described by CAS number 27119-β7-9 and/or MDL No. MFCD00084369.

In an embodiment, the interaction modulator is aminodextran. Thus, the interaction modulator, in an embodiment, is a derivative of dextran, in an embodiment of dextran as described by CAS number 9004-54-0, having a substitution degree, i.e. an average number of amino groups per monomer unit, of from 0.05 to 2, in a further embodiment of from 0.1 to 1, in a further embodiment of from 0.15 to 0.5, in a further embodiment of from about 0.2, in a further embodiment of 0.2. In a further embodiment, aminodextran has a molecular weight of from 1 kDa to 10000 kDa, in an embodiment of from 50 kDa to 5000 kDa, in a further embodiment of about 500 kDa.

In an embodiment, the interaction modulator is carboxymethyldextran. Thus, the interaction modulator, in an embodiment, is a derivative of dextran, in an embodiment of dextran as described by CAS number 9004-54-0, having a substitution degree, i.e. an average number of carboxymethyl groups per monomer unit, of from 0.05 to 2, in a further embodiment of from 0.1 to 1, in a further embodiment of from 0.15 to 0.5, in a further embodiment of from about 0.2, in a further embodiment of 0.2. In a further embodiment, carboxymethyldextran has a molecular weight of from 1 kDa to 10000 kDa, in an embodiment of from 50 kDa to 5000 kDa, in a further embodiment of about 500 kDa.

In an embodiment, the interaction modulator is triethylamine (N,N-Diethylethanamine, CAS number 121-44-8). As indicated herein above, the term, in an embodiment, includes the salts of this compound.

In an embodiment, the interaction modulator is triethanolamine (2,2',2"-Nitrilotri(ethan-1-ol), CAS number 102-71-6). As indicated herein above, the term, in an embodiment, includes the salts of this compound.

In an embodiment, the interaction modulator is Taurine (2-Aminoethane-1-sulfonic acid, CAS number 107-35-7). As indicated herein above, the term, in an embodiment, includes the salts of this compound.

In an embodiment, the interaction modulator is dodecylsulfate (lauryl sulfate), in an embodiment sodium dodecylsulfate (Sodium lauryl sulfate, CAS number 151-21-3). As indicated herein above, the term dodecylsulfate, in an embodiment, includes other salts of this compound.

In an embodiment, the interaction modulator comprises a sulfonylated compound, in an embodiment comprises PAMPS, PSSM, and/or taurine, in a further embodiment comprises PAMPS and/or PSSM, in a further embodiment comprises PAMPS and/or taurine, in a further embodiment comprises PSSM and/or taurine, in a further embodiment comprises PAMPS, in a further embodiment comprises PSSM, in a further embodiment comprises taurine. In an embodiment, the interaction modulator comprises a polycarboxylated polymeric compound, in an embodiment comprises carboxymethyldextran. In an embodiment, the interaction modulator comprises an alkylamine, in an embodiment comprises aminodextran, taurine, triethylamine, and/or triethanolamine. In an embodiment, the interaction modulator comprises a trialkylamine, in an embodiment comprises triethylamine and/or triethanolamine, in a further embodiment comprises triethylamine, in a further embodiment comprises triethanolamine. In an embodiment, the interaction modulator comprises a modulator of both a bead-enhanced and of a non-bead enhanced interaction assay, in an embodiment selected from the list consisting of aminodextran, carboxymethyldextran, triethylamine, triethanolamine, taurine, and dodecylsulfate. In an embodiment, the interaction modulator comprises a modulator specifically modulating a bead-enhanced interaction assay, in an embodiment comprises PSSM. In an embodiment, the interaction modulator comprises an enhancer of an interaction assay, in an embodiment selected from the list consisting of aminodextran, carboxymethyldextran, PAMPS, and PSSM, in a further embodiment aminodextran and/or carboxymethyldextran. In an embodiment, the interaction modulator comprises an enhancer of a bead-enhanced interaction assay, in an embodiment an enhancer specific for a bead-enhanced interaction assay, in a further embodiment PSSM; in an embodiment, said enhancer of an interaction assay is an accelerator. In an embodiment, the interaction modulator comprises an inhibitor of an interaction assay, in an embodiment selected from the list consisting of triethylamine, triethanolamine, taurine, dodecylsulfate, and PSSM, in a further embodiment selected from the list consisting of triethylamine, triethanolamine, taurine and dodecylsulfate; in an embodiment said inhibitor of an interaction assay is a retarder. In an embodiment, the interaction modulator is an enhancer at a first analyte concentration and is a retarder at a second analyte concentration, wherein said first analyte concentration is lower than the second analyte concentration, in an embodiment as specified herein above; in an embodiment, said interaction modulator being an enhancer at a first analyte concentration and being a retarder at a second analyte concentration is PSSM.

The concentration of an interaction modulator required depends on the intensity of the effect desired, the specific assay format used, including analyte and detection agent, and on further factors. The concentrations indicated herein in the Examples may be used as starting points for optimization by the skilled person.

Advantageously, it was found in the work underlying the present invention that certain chemical compounds as indicated can be used to modify kinetics and/or extent of an interaction between two binding partners in a detection reaction; in particular, it was found that some compounds are general modulators usable for bead-enhanced assays as well as non-bead enhanced assays, whereas other compounds are specific modulators. Moreover, it was surprisingly found that some compounds, in particular PSSM and PAA, have an inhibiting effect at high analyte concentrations, but an enhancing effect at low analyte concentrations and, thus, are suitable for extending the usable range of analyte concentrations in an assay.

The definitions made above apply mutatis mutandis to the following. Additional definitions and explanations made further below also apply for all embodiments described in this specification mutatis mutandis.

The present invention further relates to a kit comprising a detection agent specifically detecting an analyte in a sample, and at least one interaction modulator selected from the interaction modulators of the present invention.

The term "kit", as used herein, refers to a collection of the aforementioned compounds, means or reagents of the present invention which may or may not be packaged together. The components of the kit may be comprised by separate housings (i.e. as a kit of separate parts), or two or more components may be provided in a single housing. Moreover, it is to be understood that the kit of the present invention, in an embodiment, is to be used for practicing the methods referred to herein above. It is, in an embodiment, envisaged that components are provided in a ready-to-use manner for practicing the methods referred to above. In an embodiment, all or some of the chemical compounds of the kit are provided in dried, such as in lyophilized form, wherein the component is reconstituted using a liquid such as water or an aqueous buffered solution. In an embodiment, all or some of said compounds are provided in concentrated liquid form wherein the concentrated component is diluted using a liquid such as an aqueous buffered solution. Further, the kit, in an embodiment, contains instructions for carrying out said methods and, if applicable, said reconstitution of dried reagents. The instructions can be provided by a user's manual in paper- or electronic form. In addition, the manual may comprise instructions for interpreting the results obtained when carrying out the aforementioned methods using the kit of the present invention. In an embodiment, the kit further comprises water, a buffer, and/or a calibration reagent.

The present invention also relates to a device for determining an analyte in a sample, said device comprising an analysis unit adapted for determining a value of an interaction-related parameter in said sample and at least one interaction modulator selected from the interaction modulators of the present invention.

The term "device", as used herein, relates to a system of means comprising at least the means described, operatively linked to each other as to allow the determination. How to link the means of the device in an operating manner will depend on the type of means included into the device. In an embodiment, the means are comprised by a single device. However, it is also contemplated that the means of the current invention, e.g. the analysis unit and the evaluation unit, in an embodiment, may appear as separate devices and are, in a further embodiment, packaged together as a kit. The person skilled in the art will realize how to link the means without further ado. Preferred devices are those which can be applied without the particular knowledge of a specialized technician. In an embodiment, the device is adapted to include an additional feature as described herein. In an embodiment, the device further comprises an evaluation unit comprising a memory unit, said memory unit comprising tangibly embedded an algorithm for determining an amount of an analyte based on the results obtained by the analysis unit. In an embodiment, said algorithm is adapted for determining an amount of an analyte in the presence of at least one interaction modulator. In a further embodiment, the device further comprises (i) a display unit displaying an interaction-related parameter and/or, in an embodiment, an amount or concentration of an analyte determined; and/or comprises (ii) a memory unit storing an interaction-related parameter and/or, in an embodiment, an amount or concentration of an analyte determined. In a further embodiment, the device further comprises an output unit operatively linked at least to the evaluation unit, which output unit may be e.g. a display unit or a printer.

The device comprises an analysis unit comprising means for determining an interaction-related parameter, in particular a transmission-related parameter. Typical means and methods for determining an interaction-related parameter are known in the art. In an embodiment, the interaction-related parameter is determined with a photo-optical assay. In an embodiment, means for determining an interaction-related parameter include, in an embodiment are, means for determining a transmission-related parameter in a sample, which are known in the art and are for example described in CP Price (2001), Encyclopedia of Life Sciences, John Wiley & Sons, Ltd.: 1-7, DOI: 10.1038/npg.els.0001114; Newman et al. (1992), Ann Clin Chem 29:22). In an embodiment, a transmission-related parameter is determined by turbidimetry. Accordingly, in an embodiment, the analysis unit is adapted to measure at least one value of a transmission-related parameter of the same sample. A transmission-related parameter may be determined at one or more specific wavelength(s); thus, in an embodiment, the analysis unit comprises an optical unit, in particular a photometric unit, adapted for determining a transmission-related parameter at a wavelength of from 350 nm to 700 nm, in an embodiment of from 300 nm to 700 nm, in an embodiment of from 300 nm to 600 nm and/or of from 500 nm to 700 nm. In an embodiment, the analysis unit of the device comprises a light source irradiating the sample and a photodetector detecting light emanating from the sample, i.e. in an embodiment, detecting light passing through the sample. In a further embodiment, the analysis unit comprises a photometer unit.

Further, the present invention relates to a use of an interaction modulator for determining an analyte in an interaction assay, wherein said interaction modulator is selected from the interaction modulators of the present invention.

In an embodiment, the use is a use for inhibiting said interaction assay and wherein said interaction modulator is selected from the list consisting of triethylamine, triethanolamine, taurine, dodecylsulfate, and PSSM, in a further embodiment selected from the list consisting of triethylamine, triethanolamine, taurine and dodecylsulfate. in a further embodiment, said use is a use for enhancing said interaction assay and wherein said interaction modulator is selected from the list consisting of aminodextran, carboxymethyldextran, PAMPS, and PSSM in a further embodiment aminodextran and/or carboxymethyldextran.

Also, the present invention relates to a use of the kit according to the present invention and/or of the device according to the present invention for determining an analyte in an interaction assay.

Further, the present invention relates to a method for determining an analyte in a sample in an interaction assay, said method comprising contacting said sample with an interaction modulator, wherein said interaction modulator is an enhancer of said interaction assay at low analyte concentrations and is a retarder of said interaction assay at high analyte concentrations, and wherein said interaction modulator is Poly-(4-styrenesulfonic acid-co-maleic acid) (PSSM) and/or Polyacrylic acid (PAA).

The interaction modulators PSSM and PAA, as shown in the Examples, are interaction modulators being enhancers of interaction assays at low analyte concentrations and being retarders of interaction assays at high analyte concentrations. In an embodiment, the interaction assay is a bead-enhanced assay in such case. In an embodiment, the interaction assay is a non-competitive assay, in particular in case the interaction modulator is PAA. In an embodiment, the transmission-related parameter is not fluorescence polarization, in particular in case the interaction modulator is PAA. In an embodiment, the analyte is not an aminoglycoside, in particular in case the interaction modulator is PAA.

The terms "low analyte concentrations" and "high analyte concentrations" are relative terms, but are nonetheless understood by the skilled person. As generally understood in the art, the terms high and low concentration in the context of analytic assays relate to concentrations relative to the operation range of the particular test. Thus, in an embodiment, the term low analyte concentration relates to a concentration below the midpoint of the operation range of an assay, in an embodiment to a range between the midpoint of the operation range minus 50% of its value to the lower limit of the operation range. Analogously, in an embodiment, the term high analyte concentration relates to a concentration above the midpoint of the operation range of an assay, in an embodiment to a range between the midpoint of the operation range plus 50% of its value to the upper limit of the operation range.

In an embodiment, the dual interaction modulator is Polyacrylic acid (PAA); thus, in an embodiment, the dual interaction modulator is a polymer of acrylic acid. In a further embodiment, PAA has a repeating structural unit according to formula (II):

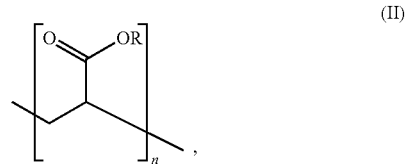

(II)

with R being H or a cation, in an embodiment an inorganic cation, in a further embodiment a cation as specified herein above. In embodiment, PAA has a molecular weight of from 1 kDa to 50 kDa, in an embodiment of from 2 kDa to 25 kDa, in a further embodiment of about 8 kDa or of about 15 kDa. In a further embodiment, the interaction modulator is the compound described by CAS number 9003-01-40 and/or MDL No. MFCD00084394.

In view of the above, the following embodiments are particularly envisaged:

1. A method for determining an analyte in a sample in an interaction assay, said method comprising contacting said sample with an interaction modulator, wherein said interaction modulator is selected from the list consisting of Poly-(4-styrenesulfonic acid-co-maleic acid) (PSSM), aminodextran, carboxymethyldextran, Poly-(2-acrylamido-2-methyl- 1-propanesulfonic acid (PAMPS), triethylamine, triethanolamine, taurine, and dodecylsulfate.

2. The method of embodiment 1, wherein said PSSM has a repeating structural unit according to formula (I):

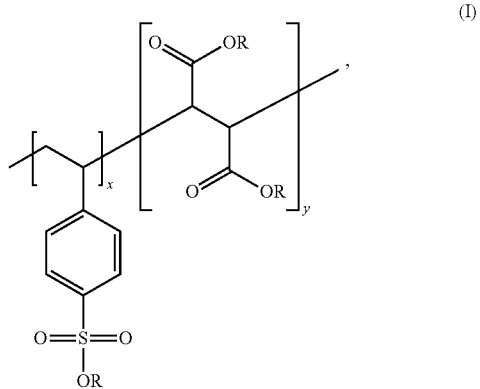

with x and y being integers selected from 0, 1, 2, 3, 4, and 5, said selection being independent for x and y and for each repeating unit; and R being H or a cation, in an embodiment an inorganic cation; and wherein said PSSM has a molecular weight of from 1 kDa to 100 kDa, in an embodiment of from 5 kDa to 50 kDa, in a further embodiment of about 20 kDa.

3. The method of embodiment 1 or 2, wherein said PSSM has a molecular weight of from 5 kDa to 50 kDa, in an embodiment of about 20 kDa.

4. The method of any one of embodiments 1 to 3, wherein said PAMPS has a repeating structural unit according to formula (III):

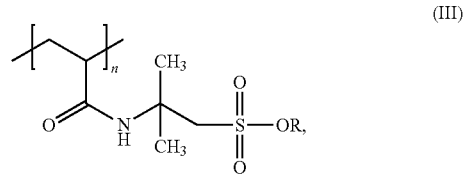

with R being H or a cation, in an embodiment an inorganic cation; and wherein said PAMPS has a molecular weight of from 100 kDa to 10000 kDa, in an embodiment of from 500 kDa to 5000 kDa, in a further embodiment of about 2000 kDa.

5. The method of any one of embodiments 1 to 4, wherein said aminodextran and said carboxymethyldextran are derivatives of dextran having a degree of substitution of from 0.05 to 2.

6. The method of any one of embodiments 1 to 5, wherein a 5% (w/v) solution of said interaction modulator in water has a density at 25° C. of from 0.8 kg/l to 1.2 kg/l, in an embodiment of from 0.9 kg/l to 1.1 kg/l, in a further embodiment of from 1.0 kg/l to 1.1 kg/l, an further embodiment of 1.05±0.2 kg/l.

7. The method of any one of embodiments 1 to 6, wherein said interaction modulator is soluble in water at a concentration of at least 5% (w/v) at a temperature of 4° C.

8. The method of any one of embodiments 1 to 7, wherein a 5% (w/v) solution of said interaction modulator has a molar extinction coefficient of less than 1000 M−1 cm−1, in a further embodiment less than 100 M−1 cm−1 at any wavelength selected from a range of from 400 nm to 700 nm, in a further embodiment of from 340 nm to 800 nm.

9. The method of any one of embodiments 1 to 8, wherein a 5% (w/v) solution of said interaction modulator has a molar extinction coefficient of less than 1000 M−1 cm−1, in a further embodiment less than 100 $M^{-1}$ $cm^{-1}$ at at least one, in an embodiment at least two, in a further embodiment at least three, in a further embodiment at least four, in a further embodiment at least five, in a further embodiment all of wavelengths 340 nm, 376 nm, 415 nm, 450 nm, 480 nm, 505 nm, 546 nm, 570 nm, 600 nm, 660 nm, 700 nm and 800 nm.

10. The method of any one of embodiments 1 to 9, wherein the viscosity of a 5% (w/v) solution of said interaction modulator is less than 15 mPas, in an embodiment is less than 10 mPas.

11. The method of any one of embodiments 1 to 10, wherein the surface tension of a 5% (w/v) solution of said interaction modulator is less than 100 mN/m, in an embodiment is less than 75 mN/m.

12. The method of any one of embodiments 1 to 11, wherein said interaction modulator comprises a sulfonylated compound, in an embodiment comprises PAMPS, PSSM, and/or taurine, in a further embodiment comprises PAMPS and/or PSSM, in a further embodiment comprises PAMPS and/or taurine, in a further embodiment comprises PSSM and/or taurine, in a further embodiment comprises PAMPS, in a further embodiment comprises PSSM, in a further embodiment comprises taurine.

13. The method of any one of embodiments 1 to 11, wherein said interaction modulator comprises a polycarboxylated polymeric compound, in an embodiment comprises carboxymethyldextran.

14. The method of any one of embodiments 1 to 11, wherein said interaction modulator comprises an alkylamine, in an embodiment comprises aminodextran, taurine, triethylamine, and/or triethanolamine.

15. The method of any one of embodiments 1 to 11, wherein said interaction modulator comprises a trialkylamine, in an embodiment comprises triethylamine and/or triethanolamine, in a further embodiment comprises triethylamine, in a further embodiment comprises triethanolamine.

16. The method of any one of embodiments 1 to 11, wherein said interaction modulator comprises a modulator of both a bead-enhanced and of a non-bead enhanced interaction assay, in an embodiment selected from the list consisting of aminodextran, carboxymethyldextran, triethylamine, triethanolamine, taurine, and dodecylsulfate.

17. The method of any one of embodiments 1 to 11, wherein said interaction modulator comprises a modulator specifically modulating a bead-enhanced interaction assay, in an embodiment comprises PSSM.

18. The method of any one of embodiments 1 to 11, wherein said interaction modulator comprises an enhancer of an interaction assay, in an embodiment selected from the list consisting of aminodextran, carboxymethyldextran, PAMPS, and PSSM, in a further embodiment aminodextran and/or carboxymethyldextran.

19. The method of any one of embodiments 1 to 11, wherein said interaction modulator comprises an enhancer of a bead-enhanced interaction assay, in an embodiment an enhancer specific for a bead-enhanced interaction assay, in a further embodiment PSSM.

20. The method of embodiment 18 or 19, wherein said enhancer of an interaction assay is an accelerator.

21. The method of any one of embodiments 1 to 11, wherein said interaction modulator comprises an inhibitor of an interaction assay, in an embodiment selected from the list consisting of triethylamine, triethanolamine, taurine, dodecylsulfate, and PSSM, in a further embodiment selected from the list consisting of triethylamine, triethanolamine, taurine and dodecyl sulfate.

22. The method of embodiment 21, wherein said inhibitor of an interaction assay is a retarder.

23. The method of any one of embodiments 1 to 11, wherein said modulator of an interaction assay is an enhancer at a first analyte concentration and is a retarder at a second analyte concentration, wherein said first analyte concentration is lower than the second analyte concentration.

24. The method of embodiment 23, wherein said interaction modulator of an interaction assay is PSSM.

26. The method of any one of embodiments 1 to 24, wherein said interaction assay is a homogenous interaction assay, in an embodiment is a homogenous immunoassay.

27. The method of any one of embodiments 1 to 26, wherein said interaction assay is an agglutination assay, in an embodiment is an agglutination immunoassay.

28. The method of any one of embodiments 1 to 27, wherein said interaction assay is a bead-enhanced agglutination assay, in a further embodiment is a latex-enhanced agglutination assay.

29. The method of any one of embodiments 1 to 28, wherein said interaction assay is a bead-enhanced agglutination immunoassay, in a further embodiment is a latex-enhanced agglutination immunoassay.

30. The method of any one of embodiments 1 to 27, wherein said interaction assay is a non-latex-enhanced agglutination assay, in a further embodiment is a non-bead-enhanced agglutination assay.

31. The method of any one of embodiments 1 to 27 or 30, wherein said interaction assay is a non-latex-enhanced agglutination immunoassay, in a further embodiment is a non-bead-enhanced agglutination immunoassay.

32. The method of any one of embodiments 1 to 31, wherein said interaction assay comprises photo-optical detection, in an embodiment is a turbidimetric or nephelometric assay.

33. The method of any one of embodiments 1 to 32, wherein said assay is an assay for C-reactive protein (CRP), in an embodiment a latex-enhanced CRP immunoassay.

34. The method of any one of embodiments 1 to 32, wherein said assay is an albumin assay, in an embodiment a non-particle-enhanced albumin immunoassay.

35. The method of any one of embodiments 1 to 34, wherein said method comprises determining a first value of an interaction-related parameter before addition of a starter compound, and determining at least one second value of an interaction-related parameter after addition of said starter compound.

36. The method of any one of embodiments 1 to 35, wherein said method comprises determining a multitude of values of a interaction-related parameter after addition of a starter compound.

37. The method of any one of embodiments 1 to 36, wherein said interaction-related parameter is a photo-optical parameter, in an embodiment is a turbidity.

38. A kit comprising a detection agent specifically detecting an analyte in a sample and at least one interaction modulator selected from the interaction modulators specified in any one of embodiments 1 to 5, 52, and 53.

39. The kit of embodiment 38, wherein said detection agent is an antibody, in an embodiment is an IgG.

40. The kit of embodiment 38 or 39, wherein said antibody is a monoclonal antibody.

41. The kit of any one of embodiments 38 to 40, wherein said detection agent is an antibody bound to a latex bead.

42. The kit of any one of embodiments 38 to 41, wherein said detection agent is a an agent comprising at least two diagnostic epitopes.

43. The kit of embodiment 42, wherein said diagnostic epitopes are identical.

44. The kit of any one of embodiments 38 to 43, further comprising water, a buffer, and/or an indicator reagent.

45. A device comprising an analyzing unit for determining an analyte in a sample, said device comprising an analysis unit adapted for determining a value of an interaction-related parameter in said sample and at least one interaction modulator selected from the interaction modulators specified in any one of embodiments 1 to 5, 52, and 53.

46. The device of embodiment 45, wherein said device further comprises an evaluation unit comprising a memory unit, said memory unit comprising tangibly embedded an algorithm for determining an amount of an analyte based on the results obtained by the analysis unit.

47. The device of embodiment 45 or 46, wherein said algorithm is adapted for determining said amount of said analyte in the presence of said at least one interaction modulator.

48. Use of an interaction modulator for determining an analyte in an interaction assay, wherein said interaction modulator is selected from the interaction modulators specified in any one of embodiments 1 to 5, 52, and 53.

49. The use of embodiment 48, wherein said use is a use for inhibiting said interaction assay and wherein said interaction modulator is selected from the list consisting of triethylamine, triethanolamine, taurine, dodecylsulfate, and PSSM, in a further embodiment selected from the list consisting of triethylamine, triethanolamine, taurine and dodecylsulfate.

50. The use of embodiment 48, wherein said use is a use for enhancing said interaction assay and wherein said interaction modulator is selected from the list consisting of aminodextran, carboxymethyldextran, PAMPS, and PSSM, in a further embodiment aminodextran and/or carboxymethyldextran.

51. Use of the kit according to any one of embodiments 38 to 44 and/or of the device according to any one of embodiments 45 to 47 for determining an analyte in an interaction assay.

52. A method for determining an analyte in a sample in an interaction assay, said method comprising contacting said sample with an interaction modulator, wherein said interaction modulator is an enhancer of said interaction assay at low analyte concentrations and is a retarder of said interaction assay at high analyte concentrations, and
wherein said interaction modulator is Poly-(4-styrenesulfonic acid-co-maleic acid) (PSSM) and/or Polyacrylic acid (PAA).

53. The method of embodiment 52, wherein said PAA has a repeating structural unit according to formula (II):

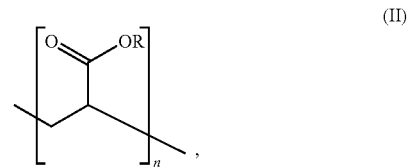

with R being H or a cation, in an embodiment an inorganic cation, and wherein said PAA has a molecular weight of from 1 kDa to 50 kDa, in an embodiment of from 2 kDa to 25 kDa, in a further embodiment of about 8 kDa or of about 15 kDa.

54. The method of embodiment 52 or 53, wherein said PSSM has a repeating structural unit according to formula (I):

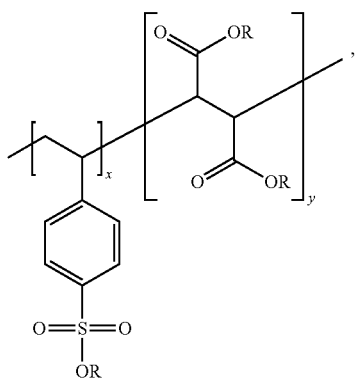

with x and y being integers selected from 0, 1, 2, 3, 4, and 5, said selection being independent for x and y and for each repeating unit; and R being H or a cation, in an embodiment an inorganic cation; and wherein said PSSM has a molecular weight of from 1 kDa to 100 kDa, in an embodiment of from 5 kDa to 50 kDa, in a further embodiment of about 20 kDa.

55. The method of any one of embodiments 52 to 54, wherein said PSSM has a molecular weight of from 5 kDa to 50 kDa, in an embodiment of about 20 kDa.

56. The method of any one of embodiments 52 to 55, wherein said PAA has a repeating structural unit according to formula (II):

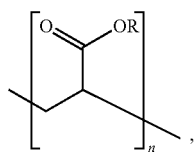

with R being H or a cation, in an embodiment an inorganic cation; and
wherein said PAA has a molecular weight of from 1 kDa to 50 kDa, in an embodiment of from 2 kDa to 25 kDa, in a further embodiment of about 8 kDa or of about 15 kDa.

57. The method of any one of embodiments 52 to 56, wherein said interaction assay is a homogenous agglutination assay, in an embodiment a homogenous agglutination immunoassay.

58. The method of any one of embodiments 52 to 57, wherein said interaction assay is a bead-enhanced agglutination assay, in a further embodiment is a latex-enhanced agglutination assay.

59. The method of any one of embodiments 52 to 58, wherein said interaction assay is a bead-enhanced agglutination immunoassay, in a further embodiment is a latex-enhanced agglutination immunoassay.

60. The method of any one of embodiments 52 to 59, wherein said assay is an assay for C-reactive protein (CRP), in an embodiment a latex-enhanced CRP immunoassay.

61. The method of any one of embodiments 52 to 60, wherein said interaction assay comprises photo-optical detection, in an embodiment is a turbidimetric or nephelometric assay.

62. The method of any one of embodiments 52 to 61, wherein said interaction modulator is present in the interaction assay mixture at a concentration of from 0.75% to 5.25%.

All references cited in this specification are herewith incorporated by reference with respect to their entire disclosure content and the disclosure content specifically mentioned in this specification.

EXAMPLES

The following Examples shall merely illustrate the invention. They shall not be construed, whatsoever, to limit the scope of the invention.

Example 1. Generic Tools and Assays 1.1 Instrument

For the experimental assessment of the modulating effect of the compounds of this invention two different turbidimetric immunoassays were applied, CRP as a latex-enhanced immunoassay and Albumin as a non-particle-enhanced immunoassay. The measurements were performed on Roche's cobas c311 analyzer, which has a multiple wavelength spectrophotometer as detection unit. The instrument automatically pipettes the sample and the assay reagents into reaction cells. Up to 3 different reagents, R1, R2 and R3, may be added to the sample. The instrument also automatically performs the mixing and incubations steps at a defined and controlled temperature (37° C.). The measuring procedure and the calculation of the measuring result also run automated. For every test, a specifically defined protocol is deposited in the analyzer software. This protocol contains the pipetting steps, the sample and reagent volumes, mixing levels, incubation times, the assay time, the measure points, the type of assay, the applied wavelength, the calibration mode and the regression equation used to generate a calibration curve for the analyte quantification.

The instrument uses a tungsten halogen lamp as irradiation source (12 V/50 W) and measures the absorbance simultaneously at 12 different wavelengths (at 340, 376, 415, 450, 480, 505, 546, 570, 600, 660, 700 and 800±2 nm) with a photodiode array consisting of 12 photodiodes. The optical path length is 5.6 mm and the optical range of the detector is 0.0000-3.0000 absorbance. The measurements are performed at 37 degrees Celsius. The analyzer generally uses one main wavelength to determine the turbidity of the assay mixture, which is generated by the agglutination reaction. A second wavelength can be used as correction wavelength. The absorbance measured by the correction wavelength is subtracted from the absorbance measured by the main wavelength. For each reaction cell, a water-blank is measured and then absorbance readings are taken 57 times in 10 minutes, here also called the complete reaction time, thus yielding a total of 57 measure points for the absorbance, also called photometric points or assay points. The assay points result in a kinetic curve for the assay, which displays the measured optical signal over the assay time. The steepness of the kinetic slope and the curve shape is thereby dependent on the assay itself and on the amount of analyte. If the assay evaluation is done by a two-point-end measurement, a sample blank is performed: Here two absorbance readings at two different measure points are considered: the first reading is usually taken before or shortly after the final reagent is added; the second reading is taken at any time point after the final reagent was added. The value obtained by subtraction of the first reading from the second reading is then the signal, here also called signal intensity, which is used to calculate the analyte amount by the involvement of the assay calibration curve.

1.2 CRP Assay

For the experimental assessment of the modulating effect of the compounds of this invention a latex-enhanced turbidimetric CRP immunoassay kit was used. Human CRP agglutinates with latex particles coated with monoclonal anti-CRP antibodies; the aggregates are determined turbidimetrically as described above. The assay kit reagents are filled in cobas c packs. These cassettes contain two reagent bottles: R1 (reaction buffer) and R2 (Latex particles coated with anti-CRP from mouse in glycine buffer).

1.3 Albumin Assay

For the experimental assessment of the modulating effect of the compounds of this invention further a non-particle-enhanced turbidimetric Albumin immunoassay kit was used. Anti-albumin antibodies react with the antigen in the sample to form antigen-antibody complexes which following agglutination are measured turbidimetrically as described above. The assay kit reagents are filled in cobas c packs. These cassettes contain two reagent bottles: R1 (reaction buffer) and R2 (polyclonal anti-human albumin antibody from sheep).

1.4 Compounds for their Assessment as Putative Kinetic Modulators

All the compounds which were assessed as assay ingredients are commercially available from suppliers of chemical reagents (Sigma Aldrich, Acros, Life Technologies, Applichem, etc.) at low costs: Triethanolamine, Triethylamine, Taurine, Sodium dodecyl sulfate (SDS), Polyacrylic acid (PAA, 8.000 Da and 15.000 Da), Aminodextran (500.000 Da), Poly-(2-acrylamide-2-methyl-1-propanesulfonic acid) (PAMPS, 2.000.000 Da), Poly-(4-styrenesulfonic acid-co-maleic acid)-sodium salt (PSSM, 20.000 Da). Only Carboxymethyldextran (500.000 Da) was prepared in-house according to standard methods.

Example 2. Enhancers for CRP Assay

For the experimental assessment of the enhancing effect of compounds of this invention different amounts of the putative signal modulator compound were added to the assay buffer R1 of the CRP assay described in chapter 1.2. As reference buffer the assay buffer R1 of the CRP assay described in chapter 1.2 was kept unchanged. All the assay buffers variations, buffers containing the putative modulator and the compound-free reference buffer, were run on cobas c311 analyzer according the assay conditions depicted in the Table 1; the reported results are the mean value of triplicate measurements. The analyte concentrations in the samples covered the measuring range of the assay, having low analyte concentration, mid analyte concentration and high analyte concentration. The signal intensity obtained for these samples using the R1 reference buffer was defined as 100% intensity. For the evaluation of the modulating effect of a compound the signal intensities obtained with the R1 buffers containing the putative accelerators were compared with the reference buffer having no modulator (100% intensity). To ensure a comparability of the signal intensities for all R1 variations identical assay points were employed for the calculation of signal intensities. A compound, increasing the signal intensity in an assay by 10% or more was defined as an enhancer.

TABLE 1

| Conditions for assessment of compounds as CRP accelerators | |
|---|---|
| Pipetting | 2 μL sample and 150 μL assay buffer (R1) are added subsequently to the reaction cell, followed by the addition of 48 μL of the latex reagent (R2), diluted with 24 μl diluent (water) |
| Assay type | Two-point-end |
| Wavelength (main/sub) | 570 nm/800 nm |
| Calibrators/calibration mode | 6 calibrators/6-point spline |
| Measuring range | 0.3-350 mg/L |
| Samples | Human serum, spiked with human CRP at concentrations covering the measuring range: Analyte-free = 0 mg/L, Low = 5 mg/L, Mid = 50 mg/L and high = 300 mg/L |
| Reaction time/assay points | 10 min/8-18 |
| R2 reagent | Latex particles coated with anti-CRP from mouse in glycine buffer 50 mmol/L, pH 8.0, immunoglobulins from mouse 0.01% and preservatives |
| R1 reagent variations | TRIS buffer 50 mmol/L, pH 7.4, with bovine serum albumin 0.15%, calcium chloride hydrate 0.2%, 1.6% sodium bromide, choline chloride 20% and preservatives (reference buffer) |
| | TRIS buffer 50 mmol/L, pH 7.4, with bovine serum albumin 0.15%, calcium chloride hydrate 0.2%, 1.6% sodium bromide, choline chloride 20% and preservatives + 0.25%, 0.5%, 0.75% or 1.0% PAMPS |
| | TRIS buffer 50 mmol/L, pH 7.4, with bovine serum albumin 0.15%, calcium chloride hydrate 0.2%, 1.6% sodium bromide, choline chloride 20% and preservatives + 0.5%, 1.0%, 2.5% or 4.0% Aminodextran (500.000 Da) |
| | TRIS buffer 50 mmol/L, pH 7.4, with bovine serum albumin 0.15%, calcium chloride hydrate 0.2%, 1.6% sodium bromide, choline chloride 20% and preservatives + 0.5%, 1.0%, 1.5% or 2.5% Carboxymethyldextran (500.000 Da) |

Figure 1B:
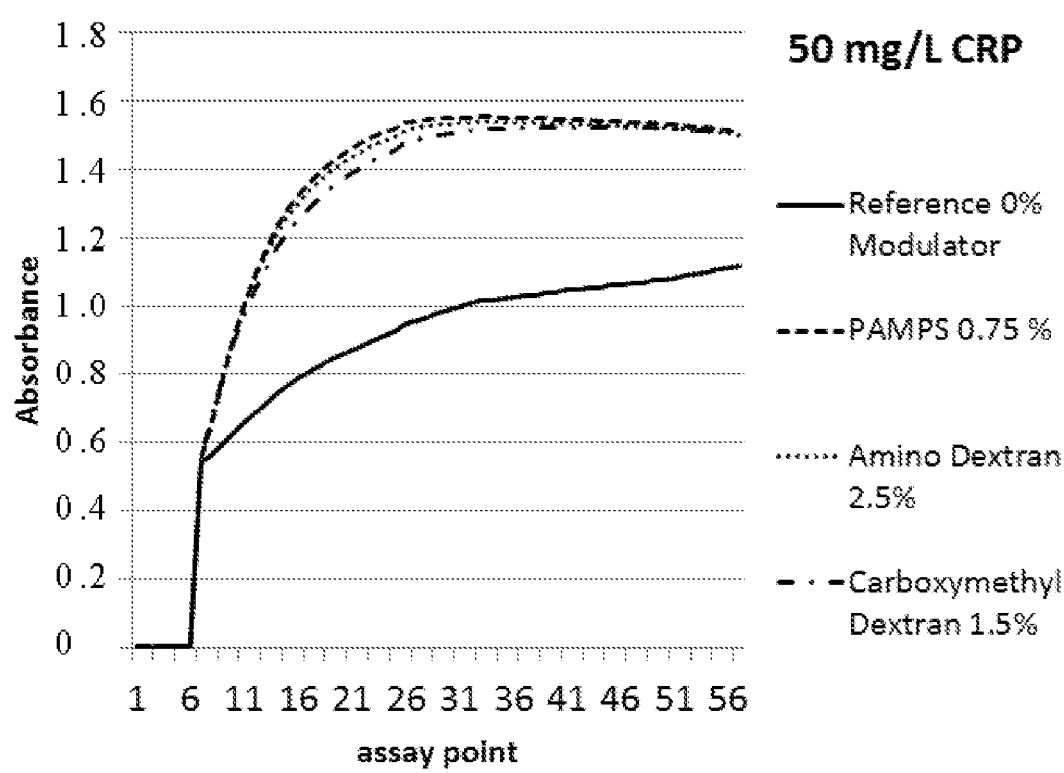
FIG. 1B: Modulator compounds as CRP-assay enhancers: change of absorbance of a homogenous CRP assay over time in a control assay or in the presence of 50 mg/L CRP as modulator.
Figure 1C:
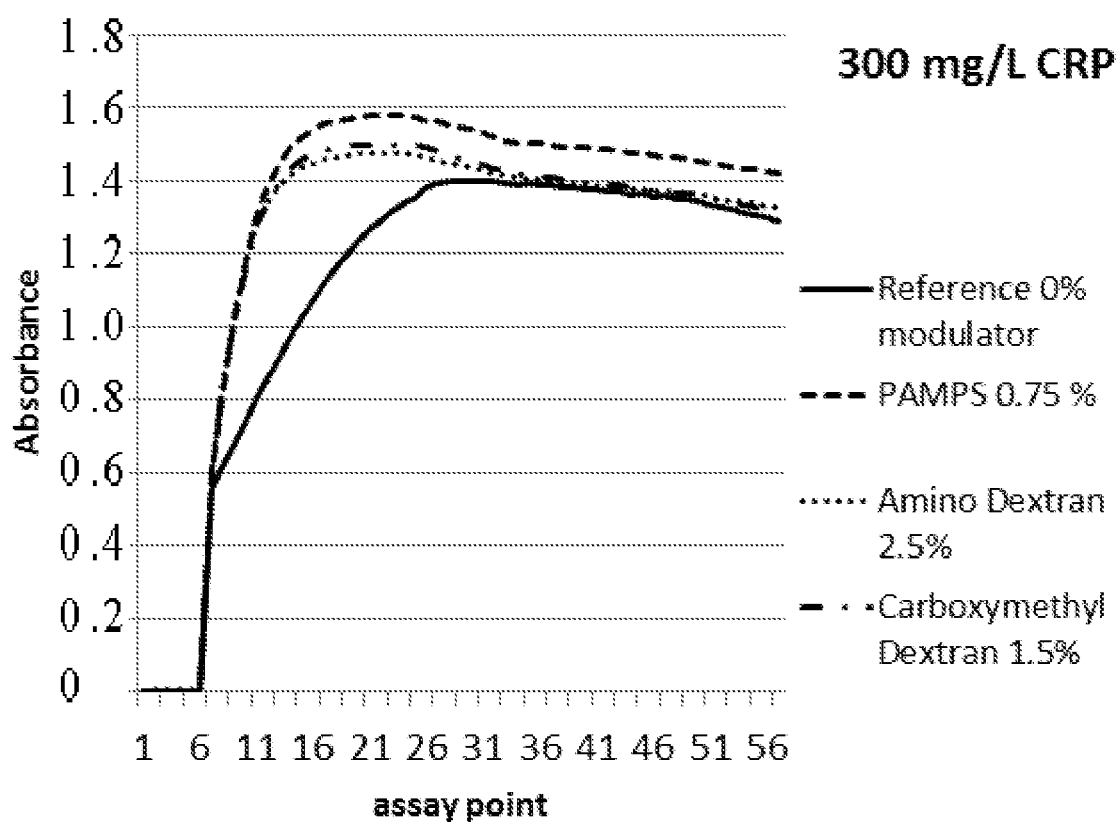
FIG. 1C: Modulator compounds as CRP-assay enhancers: change of absorbance of a homogenous CRP assay over time in a control assay or in the presence of 300 mg/L CRP as modulator.

Results:

The signal intensities found and the corresponding percent signal values (relative to reference buffer) of the assays using the modulator-containing buffers and the compound-free buffer (reference) are shown in Table 2. Poly-(2-acrylamido-2-methyl-1-propanesulfonic acid) (PAMPS, 2.000.000 Da) was applied at concentrations of 0.25%, 0.5%, 0.75% and 1%. Concentrations between 0.25% and 0.75% were found to accelerate all three tested CRP samples with concentrations at 5, 50 and 300 mg/L. 1% PAMPS was found to cause an increase in turbidity, which is not related to an analyte specific reaction. Carboxymethyldextran (500 kDa) was used in concentrations of 0.5%, 1%, 1.5% and 2.5%. Compound concentrations between 0.5% and 2.5% were found to accelerate all tested analyte concentrations. Another dextran variant, namely Aminodextran (500 kDa) was also found to be an accelerator of the CRP assay, hereby concentrations of 0.5%, 1%, 2.5% and 4% were investigated. The compound concentrations up to 2.5% were found to accelerate the signal generation for low, middle and high analyte concentrations. The signals of 4% Aminodextran were not calculated, because a non-specific agglutination reaction is observed. FIG. 1 shows the kinetic curves of the agglutination reactions facilitated by the named compounds. The kinetic curve of the concentration, which had the strongest effect, is shown. Persons, skilled in the art can obviously see that the addition of compounds resulted in a steeper curve progression in the area, where the evaluated assay points are positioned. Therefore, it is also consistent, that higher signal intensities are generated by the accelerator compounds found in said concentrations.

TABLE 2

Result overview: Modulator compounds as CRP-assay accelerators

| accelerator | Ref. without | 0.25% | 0.5% | 0.75% | 1.0% |
|---|---|---|---|---|---|
| CRP in mg/L | Abs (570-800 nm; assay points 18-8) | | | | |
| 5 | 0.048 | 0.092 | 0.143 | 0.239 | n.a. |
| 50 | 0.260 | 0.444 | 0.575 | 0.732 | |
| 300 | 0.550 | 0.759 | 0.789 | 0.756 | |
| CRP in mg/L | percentage of absorbance relative to the reference | | | | |
| 5 | 100% | 190% | 295% | 494% | n.a. |
| 50 | 100% | 171% | 222% | 282% | |
| 300 | 100% | 138% | 143% | 137% | |

| | Aminodextran T 500 in % | | | | |
|---|---|---|---|---|---|
| accelerator | Ref. without | 0.5% | 1% | 2.5% | 4% |
| CRP in mg/L | Abs (570-800 nm; assay points 18-8) | | | | |
| 5 | 0.0436 | 0.071 | 0.093 | 0.213 | n.a. |
| 50 | 0.253 | 0.339 | 0.414 | 0.692 | |
| 300 | 0.574 | 0.682 | 0.719 | 0.633 | |
| CRP in mg/L | percentage of absorbance relative to the reference | | | | |
| 5 | 100% | 162% | 213% | 488% | n.a. |
| 50 | 100% | 134% | 164% | 273% | |
| 300 | 100% | 119% | 125% | 110% | |

TABLE 2-continued

Result overview: Modulator compounds as CRP-assay accelerators

| | Carboxymethlydextran T 500 in % | | | | |
|---|---|---|---|---|---|
| accelerator | Ref. without | 0.5% | 1% | 1.5% | 2.5% |
| CRP in mg/L | Abs (570-800 nm; assay points 18-8) | | | | |
| 5 | 0.045 | 0.079 | 0.127 | 0.198 | n.a. |
| 50 | 0.251 | 0.382 | 0.498 | 0.644 | |
| 300 | 0.566 | 0.713 | 0.727 | 0.673 | |
| CRP in mg/L | percentage of absorbance relative to the reference | | | | |
| 5 | 100% | 176% | 281% | 441% | n.a. |
| 50 | 100% | 152% | 198% | 256% | |
| 300 | 100% | 126% | 129% | 119% | |

Example 3. Inhibitors for CRP Assay

For the experimental assessment of the inhibiting effect of compounds of this invention different amounts of the putative signal modulator compound were added to the assay buffer R1 of the CRP assay described in chapter 1.2. As reference buffer the assay buffer R1 of the CRP assay described in chapter 1.2 was kept unchanged. All the assay buffer variations, buffers containing the putative modulator and the compound-free reference buffer, were run on cobas c311 analyzer according the assay conditions depicted in the Table 3; the reported results are the mean value of triplicate measurements. The analyte concentrations in the samples covered the measuring range of the assay, having low analyte concentration, mid analyte concentration and high analyte concentration. The signal intensity obtained for these samples using the R1 reference buffer was defined as 100% intensity. For the evaluation of the modulating effect of a compound the signal intensities obtained with the R1 buffers containing the putative retarders were compared with the reference buffer having no modulator (100% intensity). To ensure a comparability of the signal intensities for all R1 variations identical assay points were employed for the calculation of signal intensities. A compound, decreasing the signal intensity in an assay by 10% or more was defined as an accelerator.

TABLE 3

Conditions for assessment of compounds as CRP inhibitors

| | |
|---|---|
| Pipetting | 2 μL sample and 150 μL assay buffer (R1) are added subsequently to the reaction cell, followed by the addition of 48 μL of the latex reagent (R2), diluted with 24 μl diluent (water) |
| Assay type | Two-point-end |
| Wavelength (main/sub) | 570 nm/800 nm |
| Calibrators/ calibration mode | 6 calibrators/6-point spline |
| Measuring range | 0.3-350 mg/L |
| Samples | Human serum, spiked with human CRP at concentrations covering the measuring range: Analyte-free = 0 mg/L, Low = 5 mg/L, Mid = 50 mg/L and high = 300 mg/L |
| Reaction time/assay points | 10 min/7-10 |
| R2 reagent | Latex particles coated with anti-CRP from mouse in glycine buffer 50 mmol/L, pH 8.0, immunoglobulins from mouse 0.01% and preservatives |
| R1 reagent variations | TRIS buffer 50 mmol/L, pH 7.4, with bovine serum albumin 0.15%, calcium chloride hydrate 0.2%, 0.5% PVA, 0.5% Tween 20 and preservatives (reference buffer) TRIS buffer 50 mmol/L, pH 7.4, with bovine serum albumin 0.15%, calcium chloride hydrate 0.2%, 0.5% PVA, 0.5% Tween 20 and preservatives |

TABLE 3-continued

Conditions for assessment of compounds as CRP inhibitors

+0.1%, 0.5%, 1.0%, 2.0% or 3.0% SDS
TRIS buffer 50 mmol/L, pH 7.4, with bovine serum albumin 0.15%,
calcium chloride hydrate 0.2%, 0.5% PVA, 0.5% Tween 20 and
preservatives
+0.5%, 1.0%, 2.0% or 3.0% Taurine
TRIS buffer 50 mmol/L, pH 7.4, with bovine serum albumin 0.15%,
calcium chloride hydrate 0.2%, 0.5% PVA, 0.5% Tween 20 and
preservatives
+0.1M, 0.25M, 0.5M, 0.75M or 1.0M Triethanolamine
TRIS buffer 50 mmol/L, pH 7.4, with bovine serum albumin 0.15%,
calcium chloride hydrate 0.2%, 0.5% PVA, 0.5% Tween 20 and
preservatives
+0.1M, 0.25M, 0.5M, 0.75M or 1.0M Triethylamine Results:

The signal intensities found and the corresponding percent signal values (relative to reference buffer) of the assays using the modulator-containing buffers and the compound-free buffer (reference) are shown in Table 4. SDS was investigated in concentrations of 0.1%, 0.5%, 1%, 2% and 3%. In a concentration of 3% it was also found to cause the retardation of the assay kinetics for all investigated analyte concentrations. Lower SDS concentrations, namely 1% and 2% were not applicable, because the observed signals were not correlated to the agglutination reaction. The naturally occurring amino acid Taurine was assessed in concentrations of 0.5%, 1%, 2% and 3%. From 1% concentration on a retarder activity was found for low and mid analyte concentrations. In contrast to previously published data, the group of amines, Triethanolamine and Triethylamine, was surprisingly found to be a retarder of assay kinetics.

Figure 2A:
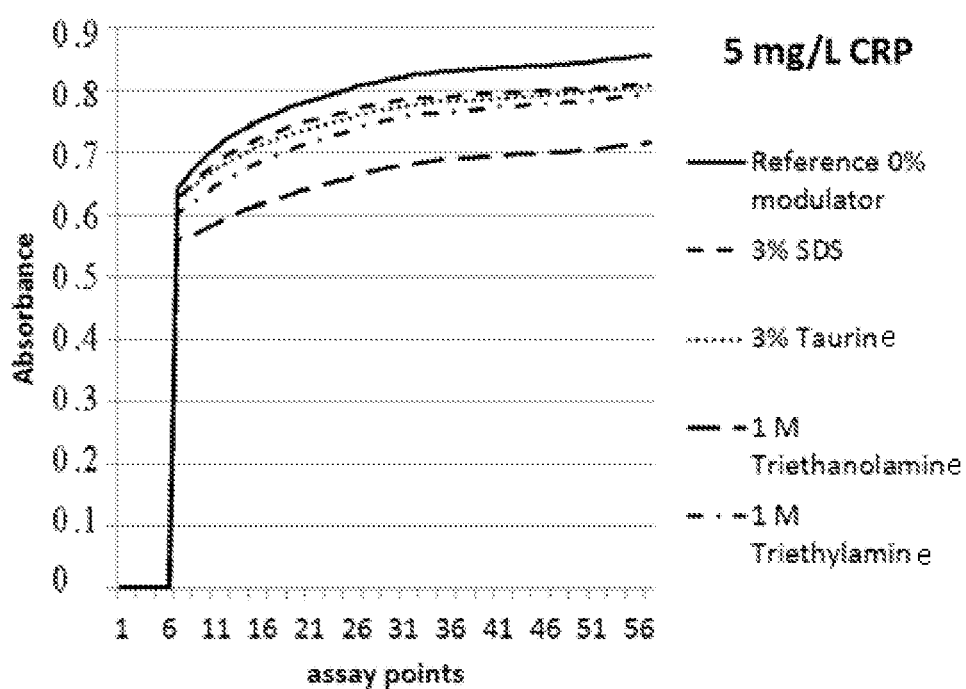
FIG. 2A: Modulator compounds as CRP-assay inhibitors: change of absorbance of a homogenous CRP assay over time in a control assay or in the presence of 5 mg/L CRP as modulator.
Figure 2B:
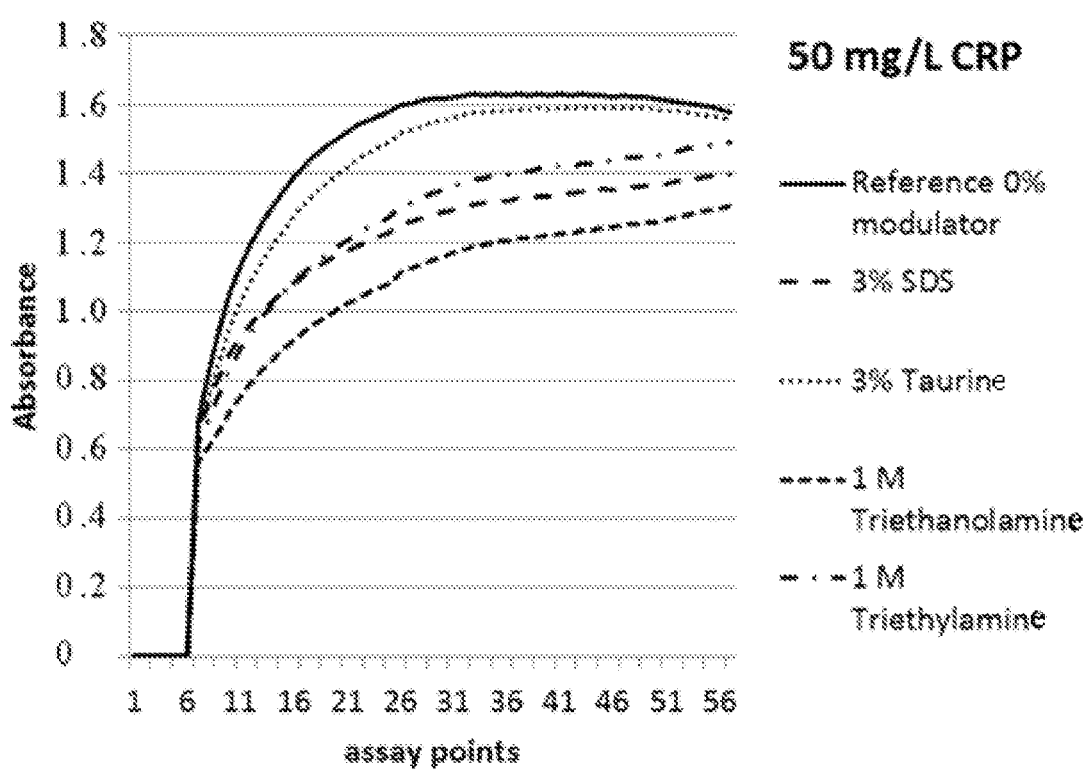
FIG. 2B: Modulator compounds as CRP-assay inhibitors: change of absorbance of a homogenous CRP assay over time in a control assay or in the presence of 50 mg/L CRP as modulator.
Figure 2C:
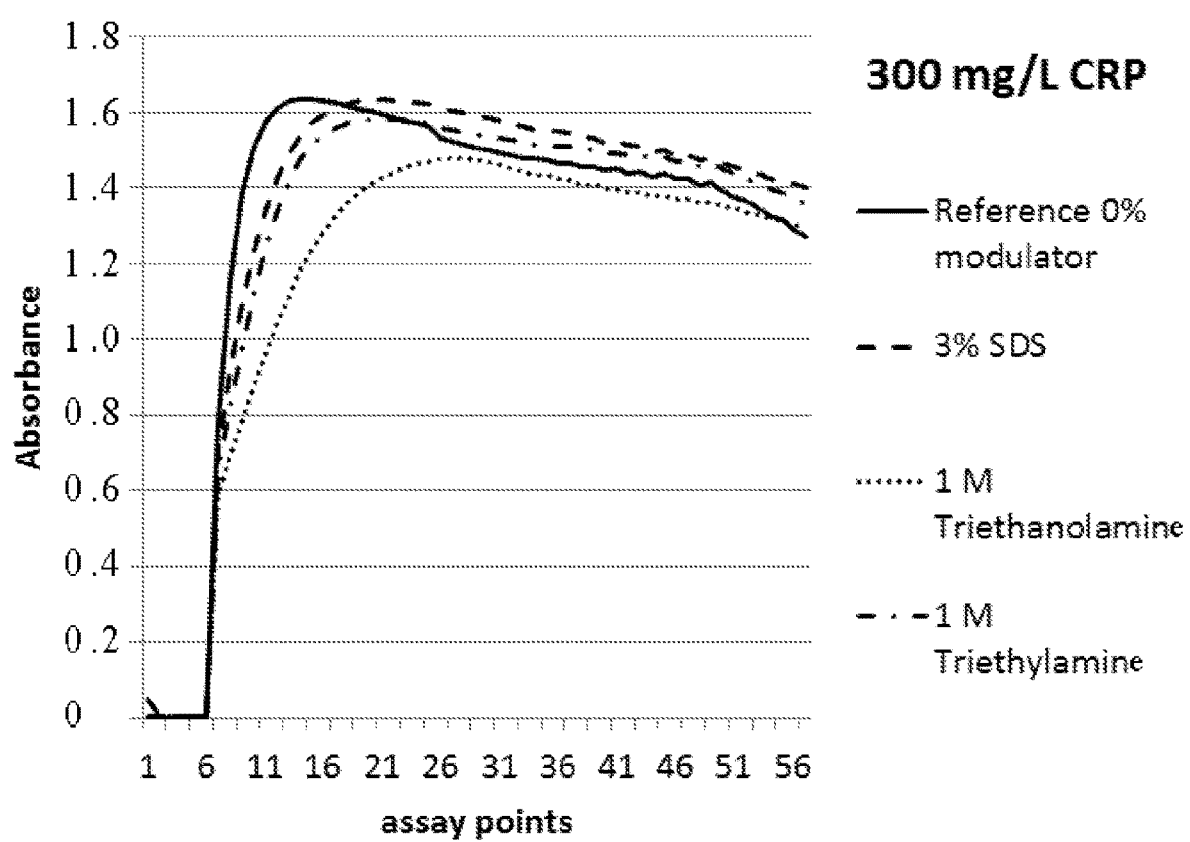
FIG. 2C: Modulator compounds as CRP-assay inhibitors: change of absorbance of a homogenous CRP assay over time in a control assay or in the presence of 300 mg/L CRP as modulator.

Triethanolamine was used at concentrations of 0.1 M, 0.25 M, 0.5 M, 0.75 M and 1 M. A retarder function was measured for concentrations of 0.25 M and higher. Hereby 0.25 M Triethanolamine retarded low and middle analyte concentrations, while higher concentrations had a retarding impact on all assessed analyte concentrations. Triethylamine was also assessed at concentrations of 0.1 M, 0.25 M, 0.5 M, 0.75 M and 1 M. A retarder function for the reaction kinetics of low, middle and high analyte concentrations was discovered for Triethylamine concentrations of 0.5 M to 1 M. Thus amines in this assay consistently display retarder functions. In FIG. 2, the kinetic curves, accelerated by the said new buffers are depicted.

TABLE 4

Result overview: Modulator compounds as CRP-assay retarders

| | SDS in % | | | | | |
|---|---|---|---|---|---|---|
| retarder | Ref. Without | 0.1% | 0.5% | 1% | 2% | 3% |
| CRP in mg/L | Abs (570-800 nm; assay points 10-7) | | | | | |
| 5 | 0.0533 | n.a. | n.a. | n.a. | n.a. | 0.044 |
| 50 | 0.3708 | | | | | 0.225 |
| 300 | 0.726 | | | | | 0.527 |
| CRP in mg/L | percentage of absorbance relative to the reference | | | | | |
| 5 | 100% | n.a. | n.a. | n.a. | n.a. | 82% |
| 50 | 100% | | | | | 61% |
| 300 | 100% | | | | | 73% |

TABLE 4-continued

Result overview: Modulator compounds as CRP-assay retarders

| | Taurine in % | | | | |
|---|---|---|---|---|---|
| retarder | Ref. Without | 0.5% | 1.0% | 2.0% | 3.0% |
| CRP in mg/L | Abs (570-800 nm; assay points 10-7) | | | | |
| 5 | 0.0556 | n.a. | 0.048 | 0.041 | 0.037 | n.a. |
| 50 | 0.3702 | | 0.348 | 0.325 | 0.301 | |
| 300 | 0.7252 | | 0.722 | 0.716 | 0.701 | |
| CRP in mg/L | percentage of absorbance relative to the reference | | | | |
| 5 | 100% | n.a. | 86% | 74% | 66% | n.a. |
| 50 | 100% | | 94% | 88% | 81% | |
| 300 | 100% | | 100% | 99% | 97% | |

| | Triethanolamine in M | | | | |
|---|---|---|---|---|---|
| retarder | Ref. without | 0.1M | 0.25M | 0.5M | 0.75M | 1M |
| CRP in mg/L | Abs (570-800 nm; assay points 10-7) | | | | |
| 5 | 0.0547 | n.a. | 0.047 | 0.040 | 0.023 | 0.019 |
| 50 | 0.3713 | | 0.296 | 0.264 | 0.164 | 0.144 |
| 300 | 0.7243 | | 0.657 | 0.600 | 0.342 | 0.286 |
| CRP in mg/L | percentage of absorbance relative to the reference | | | | |
| 5 | 100% | n.a. | 86% | 72% | 41% | 34% |
| 50 | 100% | | 80% | 71% | 44% | 39% |
| 300 | 100% | | 91% | 83% | 47% | 40% |

| | Triethylamine in M | | | | |
|---|---|---|---|---|---|
| retarder | Ref. without | 0.1M | 0.25M | 0.5M | 0.75M | 1M |
| CRP in mg/L | Abs (570-800 nm; assay points 10-7) | | | | |
| 5 | 0.0547 | n.a. | n.a. | 0.0426 | 0.0369 | 0.0316 |
| 50 | 0.3713 | | | 0.2827 | 0.2456 | 0.2143 |
| 300 | 0.7243 | | | 0.6371 | 0.5552 | 0.4648 |
| CRP in mg/L | percentage of absorbance relative to the reference | | | | |
| 5 | 100% | n.a. | n.a. | 78% | 67% | 58% |
| 50 | 100% | | | 76% | 66% | 58% |
| 300 | 100% | | | 88% | 77% | 64% |

Example 4. Enhancers for Albumin Assay

For the experimental assessment of the enhancing effect of compounds of this invention different amounts of the putative signal modulator compound were added to the assay buffer R1 of the Albumin assay described in chapter 1.3. As reference buffer the assay buffer R1 of the Albumin assay described in chapter 1.3 was kept unchanged. All the assay buffer variations, buffers containing the putative modulator and the compound-free reference buffer, were run on cobas c311 analyzer according the assay conditions depicted in the Table 5; the reported results are the mean value of triplicate measurements. The analyte concentrations in the samples covered the measuring range of the assay, having low analyte concentration, mid analyte concentration and high analyte concentration. The signal intensity obtained for these samples using the R1 reference buffer was defined as 100% intensity. For the evaluation of the modulating effect of a compound the signal intensities obtained with the R1 buffers containing the putative accelerators were compared with the reference buffer having no modulator (100% intensity). To ensure a comparability of the signal intensities for all R1 variations identical assay points were employed for the calculation of signal intensities. A compound, increasing the signal intensity in an assay by 10% or more was defined as an accelerator.

TABLE 5

| Conditions for assessment of compounds as Albumin accelerators | |
|---|---|
| Pipetting | 1.5 µL sample is diluted with 180 µL NaCl; and 1.5 µL of the diluted sample followed by 100 µL assay buffer (R1) are added subsequently to the reaction cell; finally 20 µL of the antibody reagent (R2) is added to the cell |
| Assay type | Two-point-end |
| Wavelength (main/sub) | 340 nm/700 nm |
| Calibrators/calibration mode | 6 calibrators/RCM (Rodbard) |
| Measuring range of assay | 3-96 g/L |
| Samples | Human serum, spiked with human albumin at concentrations covering the measuring range: Analyte-free = 0 g/L, Low = 5 g/L, Mid = 50 g/L and High = 100 g/L |
| Reaction time/assay points | 10 min/6-9 |
| R2 reagent | polyclonal anti-human albumin antibody from sheep, TRIS buffer 100 mmol/L, pH 7.2, preservatives |
| R1 reagent variations | TRIS buffer 50 mmol/L, pH 8.0, Tween 20 1%, EDTA 2.0 mmol/L, preservatives (reference buffer) TRIS buffer 50 mmol/L, pH 8.0, Tween 20 1%, EDTA 2.0 mmol/L, preservatives +0.5%, 1.0%, 2.5% or 4.0% Aminodextran (500.000 Da) TRIS buffer 50 mmol/L, pH 8.0, Tween 20 1%, EDTA 2.0 mmol/L, preservatives +0.5%, 1.0%, 1.5% or 2.5% Carboxymethyldextran (500.000 Da) |

Figure 3A:
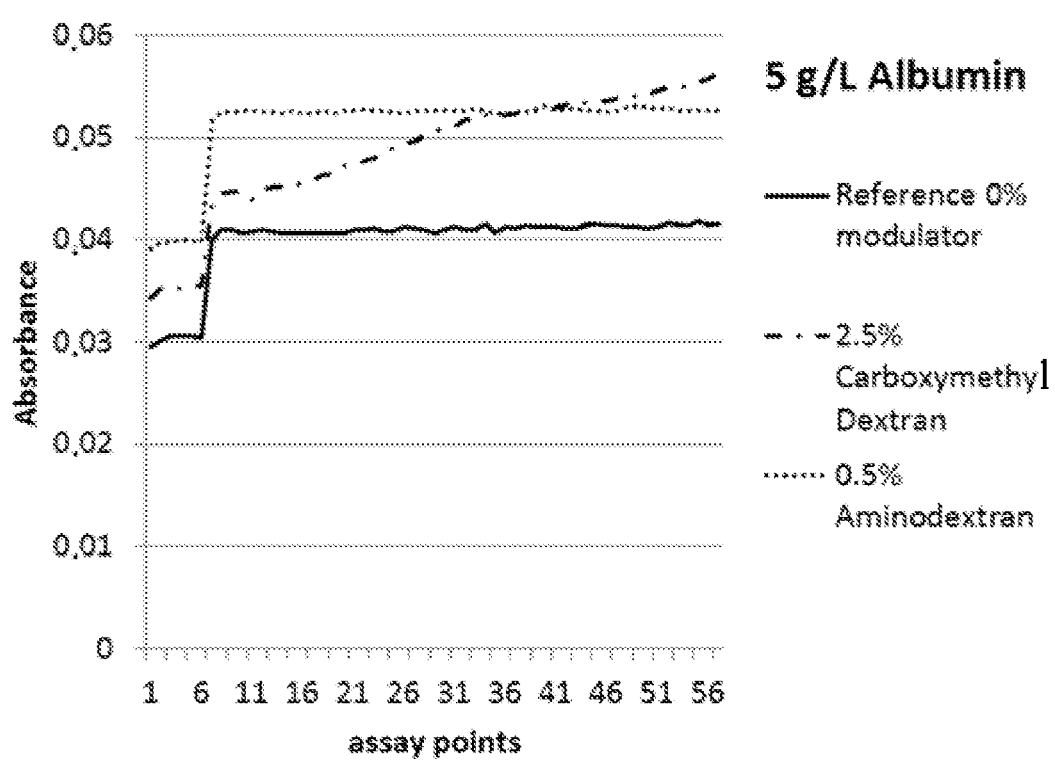
FIG. 3A: Modulator compounds as Albumin assay enhancers: change of absorbance of a homogenous albumin assay over time in a control assay or in the presence of 5 g/L albumin as modulator.
Figure 3B:
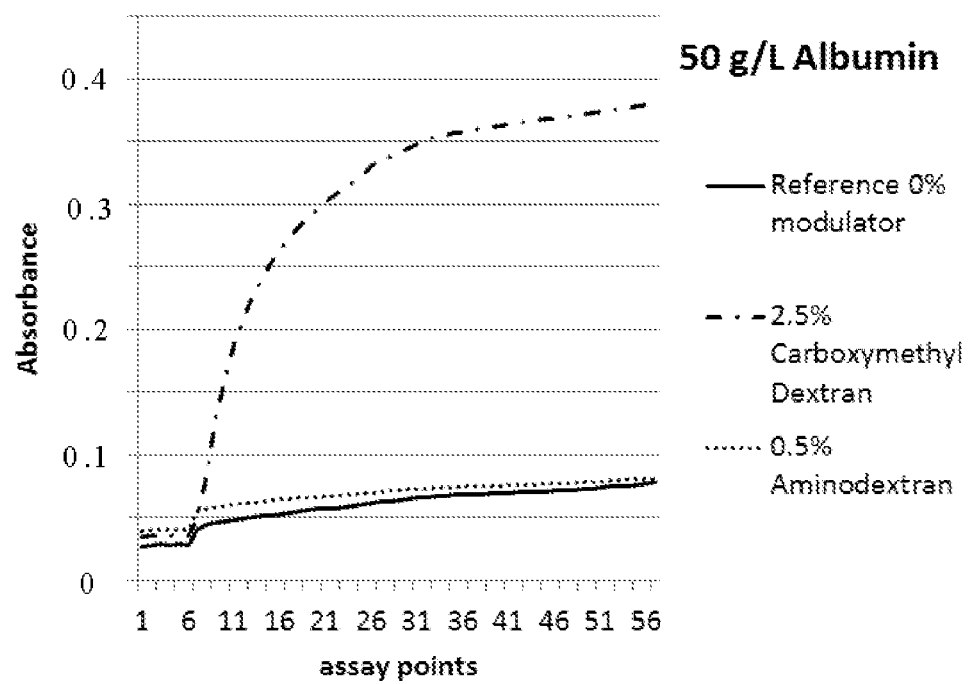
FIG. 3B: Modulator compounds as Albumin assay enhancers: change of absorbance of a homogenous albumin assay over time in a control assay or in the presence of 50 g/L albumin as modulator.
Figure 3C:
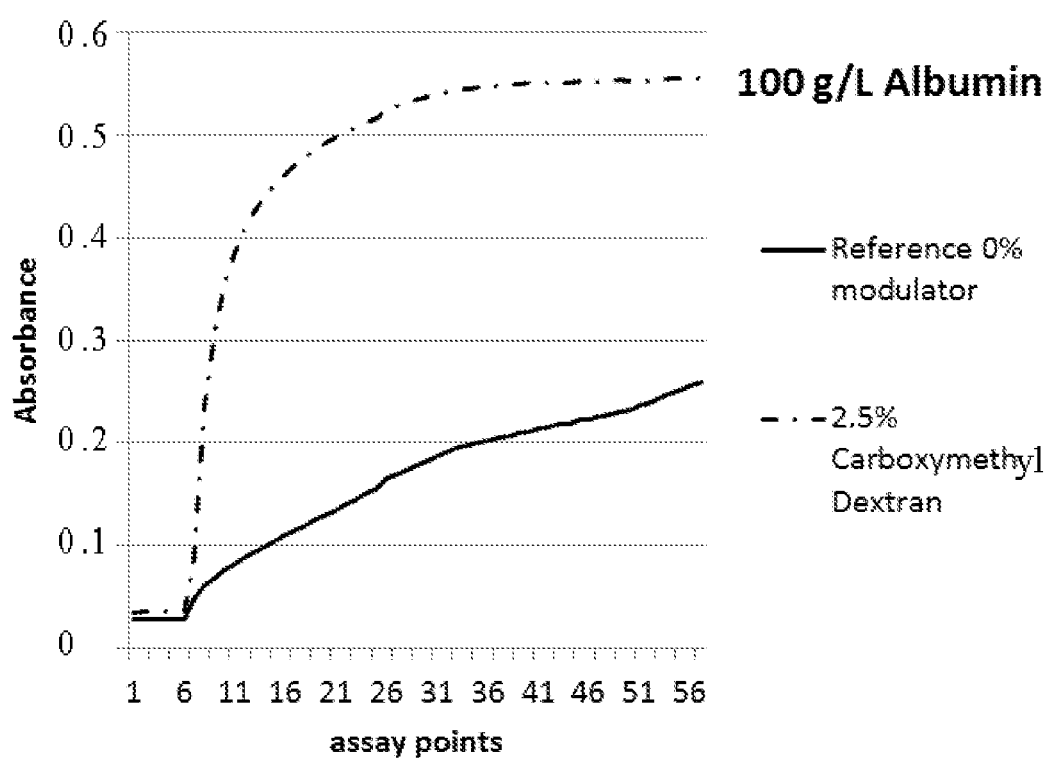
FIG. 3C: Modulator compounds as Albumin assay enhancers: change of absorbance of a homogenous albumin assay over time in a control assay or in the presence of 300 g/L albumin as modulator.

Results:

The signal intensities found and the corresponding percent signal values (relative to reference buffer) of the assays using the modulator-containing buffers and the compound-free buffer (reference) are shown in Table 6. The Albumin assay is a non-particle-enhanced immunoassay, which means, that the slope of the assay kinetic is flatter than the slope of the kinetic of a particle-enhanced immunoassay. This fact has especially to be taken in account, when evaluating the kinetics of low analyte concentration 5 g/L for the buffer variant containing the Carboxymethyldextran as modulator. A person, skilled in the art will clearly see that in FIG. 3 in the graph for 5 g/L albumin, the kinetic of the Carboxymethyldextran containing buffer is steeper than the kinetic of the reference without modulator. However, when the buffer containing Carboxymethyldextran was evaluated using assay points 9-6, 5 g/L were quantified to be only 82% relative to the reference without modulator. Therefore, other assay points than 6-9 are used to assess the properties of Carboxymethyldextran, namely AP 7-10 (data shown in Table 6). The compound Carboxymethyldextran was added to the Albumin assay in concentrations of 0.5%, 1%, 1.5% and 2.5%. An acceleration of the reaction was found for the concentration of 2.5%. Hereby the employment of suitable assay points showed the acceleration of the reaction kinetics of low, mid and high albumin concentrations. The compound Aminodextran was used in concentrations of 0.5%, 1%, 2.5% and 4%. Here it was found, that the smallest compound concentration of 0.5 Aminodextran was found to accelerate only low and mid analyte concentrations. The kinetic curves for selected concentrations of the compounds are depicted in FIG. 3.

TABLE 6

Result overview: Modulator compounds as Albumin assay accelerators

| accelerator | Carboxymethyldextran T 500 in % | | | | |
|---|---|---|---|---|---|
| | Ref. Without | 0.50% | 1.00% | 1.50% | 2.50% |
| ALB in g/L | Abs (340-700 nm; assay points 10-7) | | | | |
| 5 | 0.0007 | n.a. | n.a. | n.a. | 0.0012 |
| 50 | 0.007 | | | | 0.1119 |
| 100 | 0.0276 | | | | 0.27 |

TABLE 6-continued

Result overview: Modulator compounds as Albumin assay accelerators

| ALB in g/L | percentage of absorbance relative to the reference | | | | |
|---|---|---|---|---|---|
| 5 | 100% | n.a. | n.a. | n.a. | 171% |
| 50 | 100% | | | | 1599% |
| 100 | 100% | | | | 978% |

| accelerator | Aminodextran T 500 in % | | | | |
|---|---|---|---|---|---|
| | Ref. Without | 0.50% | 1.00% | 2.50% | 4.00% |
| ALB in g/L | Abs (340-700 nm; assay points 9-6) | | | | |
| 5 | 0.0102 | 0.0127 | n.a. | n.a. | n.a. |
| 50 | 0.0164 | 0.0184 | | | |
| 100 | 0.0393 | 0.0401 | | | |

| ALB in g/L | percentage of absorbance relative to the reference | | | | |
|---|---|---|---|---|---|
| 5 | 100% | 125% | n.a. | n.a. | n.a. |
| 50 | 100% | 112% | | | |
| 100 | 100% | 102% | | | |

Example 5. Inhibitors for Albumin Assay

For the experimental assessment of the inhibiting effect of compounds of this invention different amounts of the putative signal modulator compound were added to the assay buffer R1 of the Albumin assay described in chapter 1.3. As reference buffer the assay buffer R1 of the Albumin assay described in chapter 1.3 was kept unchanged. All the assay buffer variations, buffers containing the putative modulator and the compound-free reference buffer, were run on cobas c311 analyzer according the assay conditions depicted in the Table 7; the reported results are the mean value of triplicate measurements. The analyte concentrations in the samples covered the measuring range of the assay, having low analyte concentration, mid analyte concentration and high analyte concentration. The signal intensity obtained for these samples using the R1 reference buffer was defined as 100% intensity. For the evaluation of the modulating effect of a compound, the signal intensities obtained with the R1 buffers containing the putative decelerators were compared with the reference buffer having no modulator (100% intensity). To ensure a comparability of the signal intensities for all R1 variations identical assay points were employed for the calculation of signal intensities. A compound decreasing the signal intensity in an assay by 10% or more was defined as a retarder.

TABLE 7

Conditions for assessment of compounds as Albumin retarders

| | |
|---|---|
| Pipetting | 1.5 µL sample is diluted with 180 µL NaCl; and 1.5 µL of the diluted sample followed by 100 µL assay buffer (R1) are added subsequently to the reaction cell; finally 20 µL of the antibody reagent (R2) is added to the cell |
| Assay type | Two-point-end |
| Wavelength (main/sub) | 340 nm/700 nm |
| Calibrators/calibration mode | 6 calibrators/RCM (Rodbard) |
| Measuring range of assay | 3-96 g/L |
| Samples | Human serum, spiked with human albumin at concentrations covering the measuring range: Analyte-free = 0 g/L, Low = 5 g/L, Mid = 50 g/L and High = 100 g/L |

TABLE 7-continued

Conditions for assessment of compounds as Albumin retarders

| | |
|---|---|
| Reaction time/assay points | 10 min/6-9 |
| R2 reagent | polyclonal anti-human albumin antibody from sheep, TRIS buffer 100 mmol/L, pH 7.2, preservatives |
| R1 reagent variations | TRIS buffer 50 mmol/L, pH 8.0, Tween 20 1%, PEG 4%, preservatives (reference buffer)<br>TRIS buffer 50 mmol/L, pH 8.0, Tween 20 1%, PEG 4%, preservatives<br>+0.25%, 0.5%, 0.75% or 1.0% PAMPS<br>TRIS buffer 50 mmol/L, pH 8.0, Tween 20 1%, PEG 4%, preservatives<br>+0.05M, 0.1M, 0.25M, 0.5M Triethanolamine<br>TRIS buffer 50 mmol/L, pH 8.0, Tween 20 1%, PEG 4%, preservatives<br>+0.05M, 0.1M, 0.25M, 0.5M Triethylamine<br>TRIS buffer 50 mmol/L, pH 8.0, Tween 20 1%, PEG 4%, preservatives<br>+0.5%, 1.0%, 2.0% or 3.0% Taurine<br>TRIS buffer 50 mmol/L, pH 8.0, Tween 20 1%, PEG 4%, preservatives<br>+0.5%, 1.0%, 2.0% or 3.0% SDS<br>TRIS buffer 50 mmol/L, pH 8.0, Tween 20 1%, PEG 4%, preservatives<br>+0.5%, 1.0%, 2.5% or 4.0% Aminodextran (500.000 Da) |

Figure 4A:
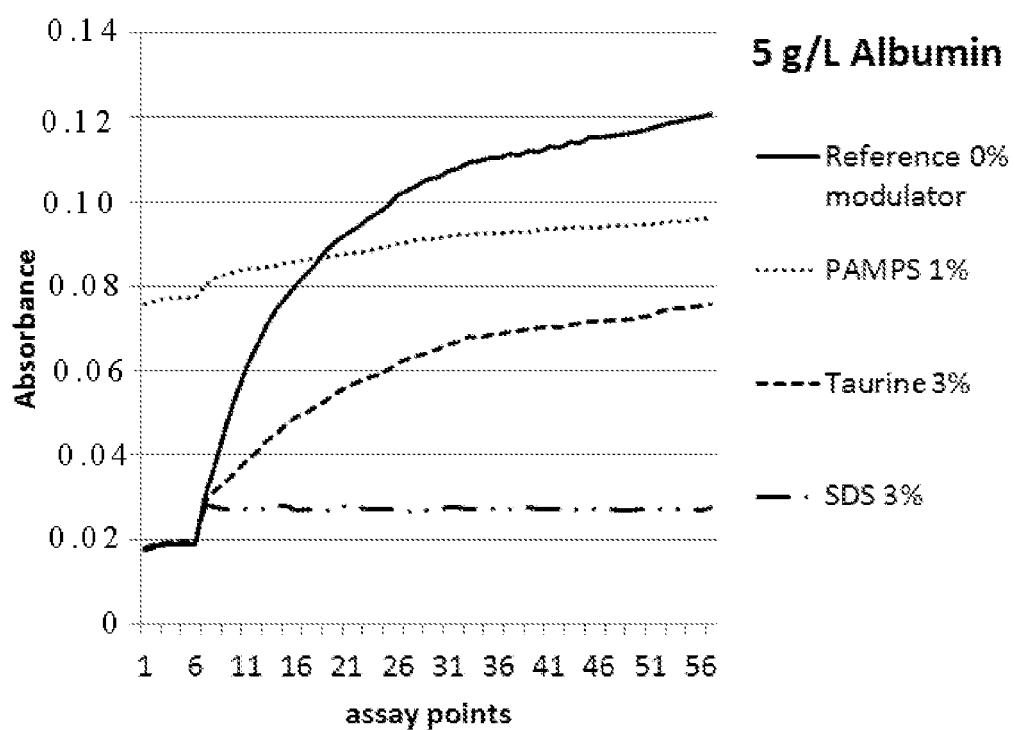
FIG. 4A: Modulator compounds as Albumin assay inhibitors: change of absorbance of a homogenous albumin assay over time in a control assay or in the presence of 5 g/L albumin as modulator.
Figure 4B:
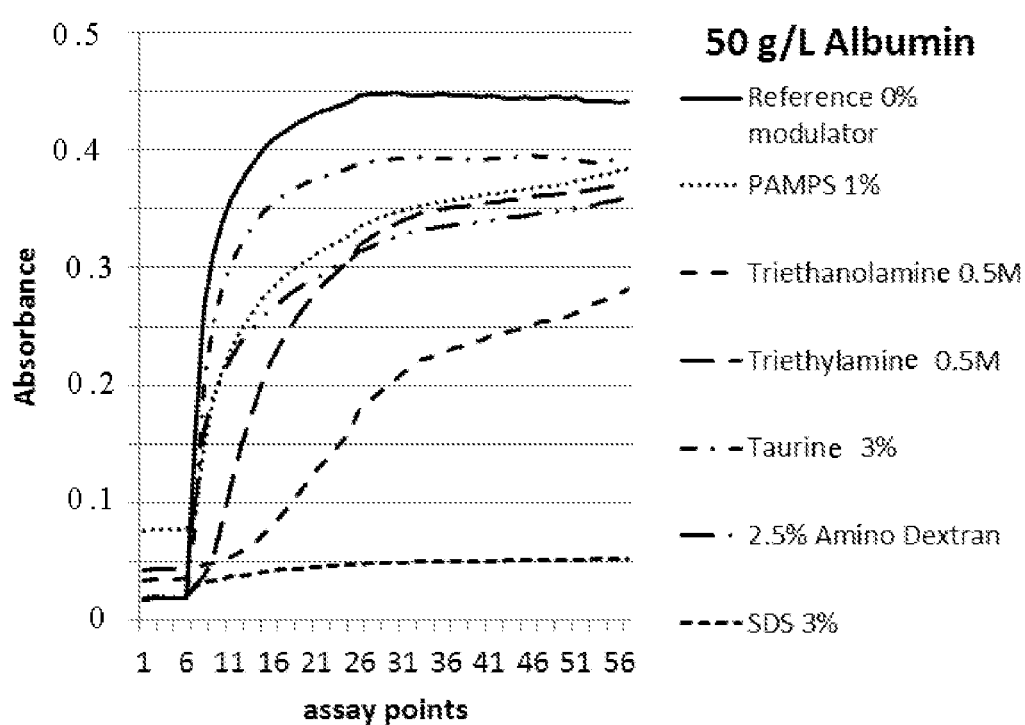
FIG. 4B: Modulator compounds as Albumin assay inhibitors: change of absorbance of a homogenous albumin assay over time in a control assay or in the presence of the 50 g/L albumin as modulator.
Figure 4C:
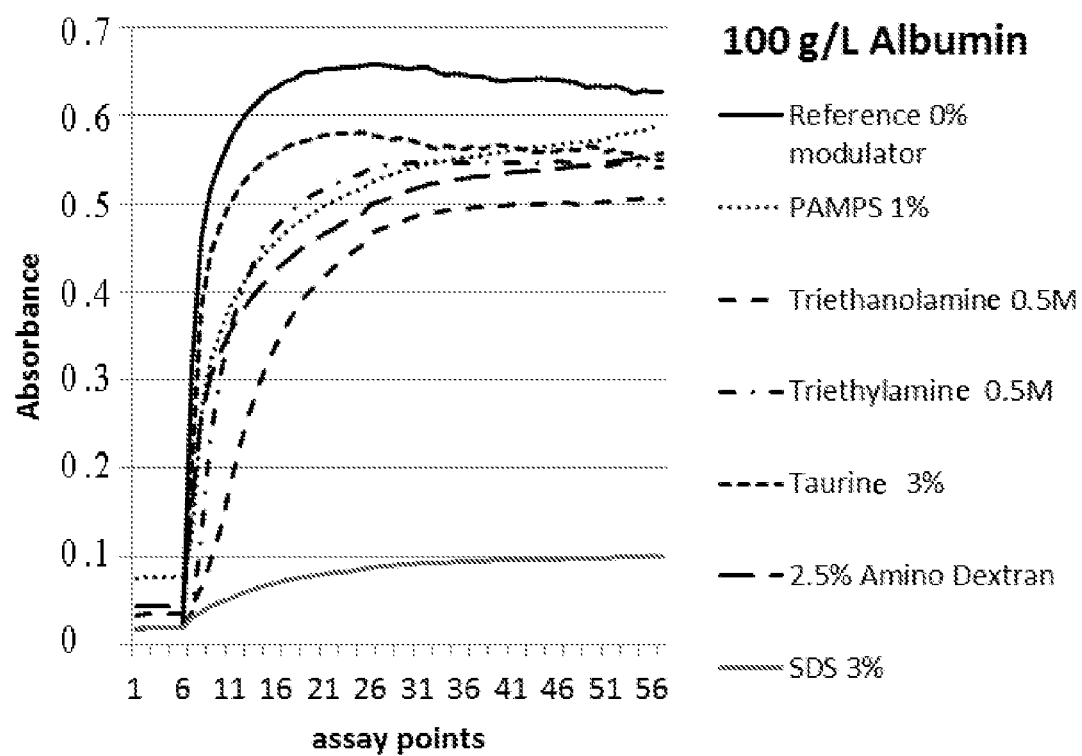
FIG. 4C: Modulator compounds as Albumin assay inhibitors: change of absorbance of a homogenous albumin assay over time in a control assay or in the presence of 300 g/L albumin as modulator.

Results:

The signal intensities found and the corresponding percent signal values (relative to reference buffer) of the assays using the modulator-containing buffers and the compound-free buffer (reference) are shown in Table 8. PAMPS was used in concentrations of 0.25%, 0.5%, 0.75% and 1%, and all employed concentrations functioned as retarder for low, mid and high albumin concentrations. Higher PAMPS concentrations also resulted in a stronger retardation of assay kinetics. We also found decelerating effect when using the R1 buffers containing the amine compounds. Triethanolamine was investigated at concentration of 0.05 M, 0.1 M, 0.25 M and 0.5 M. For 0.25 M and 0.5 M were found retarding activity for mid and high concentrations. Triethylamine was investigated in concentrations of 0.05 M, 0.1 M, 0.25 M and 0.5 M. Here, the highest concentration of 0.5 M resulted in the retardation of the assay kinetics for mid and high albumin concentrations. Finally, Taurine was assessed in concentrations of 0.5%, 1%, 2% and 3%. The buffer with 3% Taurine decelerates the kinetic curve of high, mid and high albumin concentrations. Finally, addition of SDS to the assay buffers was also found to decelerate the assay kinetics. SDS concentrations of 0.5%, 1%, 2% and 3% were used. The concentrations between 1% and 3% succeeded in the retardation of the reaction kinetics of low, middle and high albumin concentrations. In the case of the retarder candidates for the Albumin assay, we observed, that the pH adjustment resulted in the generation of NaCl. This NaCl turned out to have a retarder-effect itself. We calculated the retarder-effect, contributed by NaCl in order to recalculate the percent values of the retarder compounds of the Albumin assay. This procedure enabled us to show the values for the compounds, which are devoid of the NaCl-retarder-effect. Aminodextran shows an interesting behavior: depending on the formulation of the buffer R1 it shows either an accelerating (see Table 6, R1: TRIS buffer 50 mmol/L, pH 8.0, Tween 20 1%, EDTA 2.0 mmol/L, preservatives, Aminodextran) or decelerating (Table 8, R1: TRIS buffer 50 mmol/L, pH 8.0, Tween 20 1%, PEG 4%, preservatives, Aminodextran) effect, probably due to synergistic effects with the buffer components. In FIG. 4 the kinetic curves obtained with the new buffers are shown.

TABLE 8

Result overview: Modulator compounds as Albumin assay retarders

| retarder | PAMPS in % | | | | |
|---|---|---|---|---|---|
| | Ref. without | 0.25% | 0.50% | 0.75% | 1.00% |
| ALB in g/L | Abs (340-700 nm; assay points 9-6) | | | | |
| 5 | 0.028 | 0.018 | 0.012 | 0.009 | 0.006 |
| 50 | 0.291 | 0.173 | 0.147 | 0.126 | 0.109 |
| 100 | 0.499 | 0.327 | 0.293 | 0.268 | 0.244 |
| ALB in g/L | percentage of absorbance relative to the reference (NaCl effect corr.) | | | | |
| 5 | 100% | 78% | 60% | 47% | 37% |
| 50 | 100% | 55% | 46% | 39% | 33% |
| 100 | 100% | 58% | 51% | 46% | 41% |

| retarder | Triethanolamine in M | | | | |
|---|---|---|---|---|---|
| | Ref. without | 0.05M | 0.1M | 0.25M | 0.5M |
| ALB in g/L | Abs (340-700 nm; assay points 9-6) | | | | |
| 5 | 0.0275 | n.a. | n.a. | 0.009 | 0.007 |
| 50 | 0.2858 | | | 0.045 | 0.013 |
| 100 | 0.4982 | | | 0.255 | 0.058 |
| ALB in g/L | percentage of absorbance relative to the reference | | | | |
| 5 | 100% | n.a. | n.a. | 96% | 92% |
| 50 | 100% | | | 71% | 71% |
| 100 | 100% | | | 86% | 53% |

| retarder | Triethylamine | | | | |
|---|---|---|---|---|---|
| | Ref. without | 0.05M | 0.1M | 0.25M | 0.5M |
| ALB in g/L | Abs (340-700 nm; assay points 9-6) | | | | |
| 5 | 0.029 | n.a. | n.a. | n.a. | 0.009 |
| 50 | 0.296 | | | | 0.034 |
| 100 | 0.511 | | | | 0.216 |

TABLE 8-continued

Result overview: Modulator compounds as Albumin assay retarders

| ALB in g/L | percentage of absorbance relative to the reference (NaCl effect corr.) | | | | |
|---|---|---|---|---|---|
| 5 | 100% | n.a. | n.a. | n.a. | 99% |
| 50 | 100% | | | | 78% |
| 100 | 100% | | | | 83% |

| | Taurine in % | | | | |
|---|---|---|---|---|---|
| retarder | Ref. without | 0.5% | 1% | 2% | 3% |
| ALB in g/L | Abs (340-700 nm; assay points 9-6) | | | | |
| 5 | 0.028 | n.a. | n.a. | n.a. | 0.014 |
| 50 | 0.291 | | | | 0.231 |
| 100 | 0.499 | | | | 0.424 |

| ALB in g/L | percentage of absorbance relative to the reference (NaCl effect corr.) | | | | |
|---|---|---|---|---|---|
| 5 | 100% | n.a. | n.a. | n.a. | 67% |
| 50 | 100% | | | | 75% |
| 100 | 100% | | | | 77% |

| | SDS in % | | | | |
|---|---|---|---|---|---|
| retarder | Ref. without | 0.5% | 1% | 2% | 3% |
| ALB in g/L | Abs (340-700 nm; assay points 9-6) | | | | |
| 5 | 0.0339 | n.a. | 0.0111 | 0.0088 | 0.0084 |
| 50 | 0.2841 | | 0.0813 | 0.018 | 0.0143 |
| 100 | 0.4758 | | 0.2319 | 0.0354 | 0.0242 |

| ALB in g/L | percentage of absorbance relative to the reference (NaCl effect corr.) | | | | |
|---|---|---|---|---|---|
| 5 | 100% | n.a. | 60% | 54% | 67% |
| 50 | 100% | | 30% | 8% | 9% |
| 100 | 100% | | 47% | 6% | 5% |

| | Aminodextran T 500 in % | | | | |
|---|---|---|---|---|---|
| retarder | Ref. without | 0.5% | 1% | 2.5% | 4% |
| ALB in g/L | Abs (340-700 nm; assay points 9-6) | | | | |
| 5 | 0.0283 | 0.0289 | 0.0286 | 0.0239 | 0.0213 |
| 50 | 0.293 | 0.1316 | 0.1234 | 0.1458 | 0.1682 |
| 100 | 0.4998 | 0.2513 | 0.2267 | 0.2596 | 0.3076 |

| ALB in g/L | percentage of absorbance relative to the reference (NaCl effect corr.) | | | | |
|---|---|---|---|---|---|
| 5 | 100% | 125% | 126% | 114% | 109% |
| 50 | 100% | 47% | 44% | 53% | 62% |
| 100 | 100% | 49% | 44% | 51% | 62% |

Example 6. Dual Modulators for CRP Assay

During the experiments with the CRP assay described in the chapters 2 and 3 we found surprising results when using three compounds as assay ingredients:

We found that the compounds Poly-(4-styrenesulfonic acid-co-maleic acid)-sodium salt (PSSM, 20.000 Da), Poly-acrylic acid (PAA, 8.000 Da) and PAA (15.000 Da) to possess unexpected, however very beneficial properties in terms of immunoassay modulation. So far, one would have expected that one compound will show a unidirectional effect on the kinetics of immunoassays. More precisely, this means one compound would either accelerate or decelerate an immunoassay. Here, it was found that one compound can actually do both in one and the same buffer: it accelerates low analyte concentrations and it retards mid and high analyte concentrations, thus having the potential to increase the analytical sensitivity and the upper detection limit. Here we could find such a dual modulating activity of the compounds in the two different ground buffer formulations, R1a and R1b (see Table 9 and 10), used for accelerator and retarder assessment in the CRP assay from chapters 2 and 3. The found signal intensities and the corresponding percent signal values (relative to reference buffer R1a or R1b) of the assays using the modulator-containing buffers and the compound-free buffer (reference) are shown in Table 11.

Figure 5A:
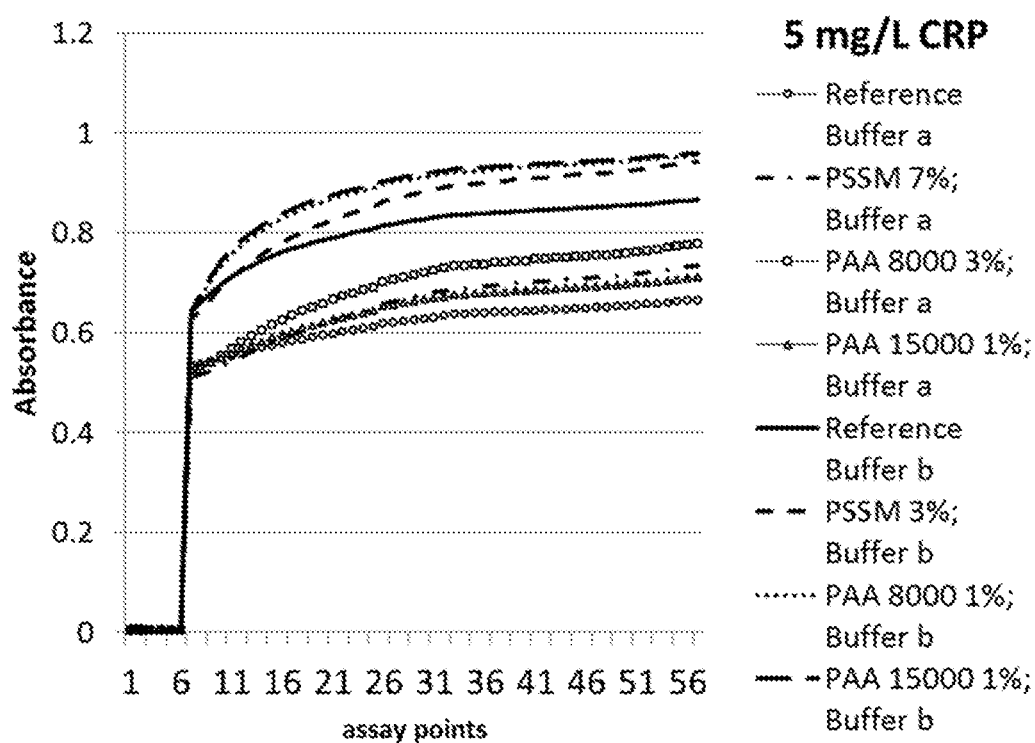
FIG. 5A: Modulator compounds as CRP-assay dual modulators: change of absorbance of a homogenous CRP assay over time in a control assay or in the presence of 5 mg/L CRP, B) 50 mg/L CRP as modulator.
Figure 5B:
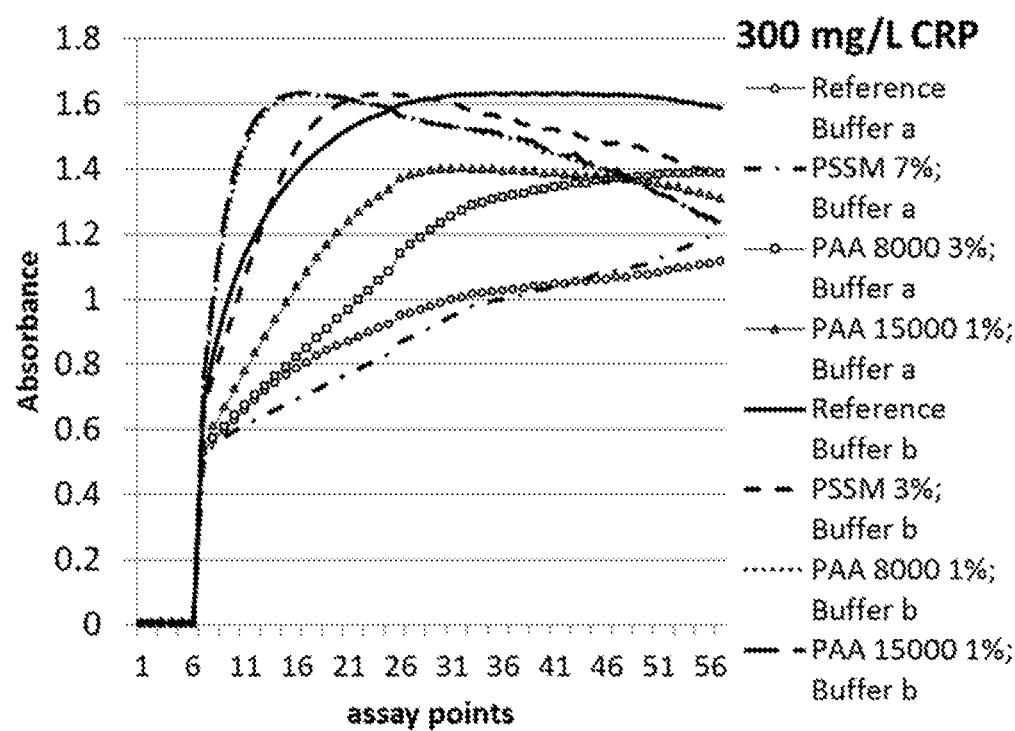
FIG. 5B: Modulator compounds as CRP-assay dual modulators: change of absorbance of a homogenous CRP assay over time in a control assay or in the presence of 50 mg/L CRP as modulator.
Figure 5C:
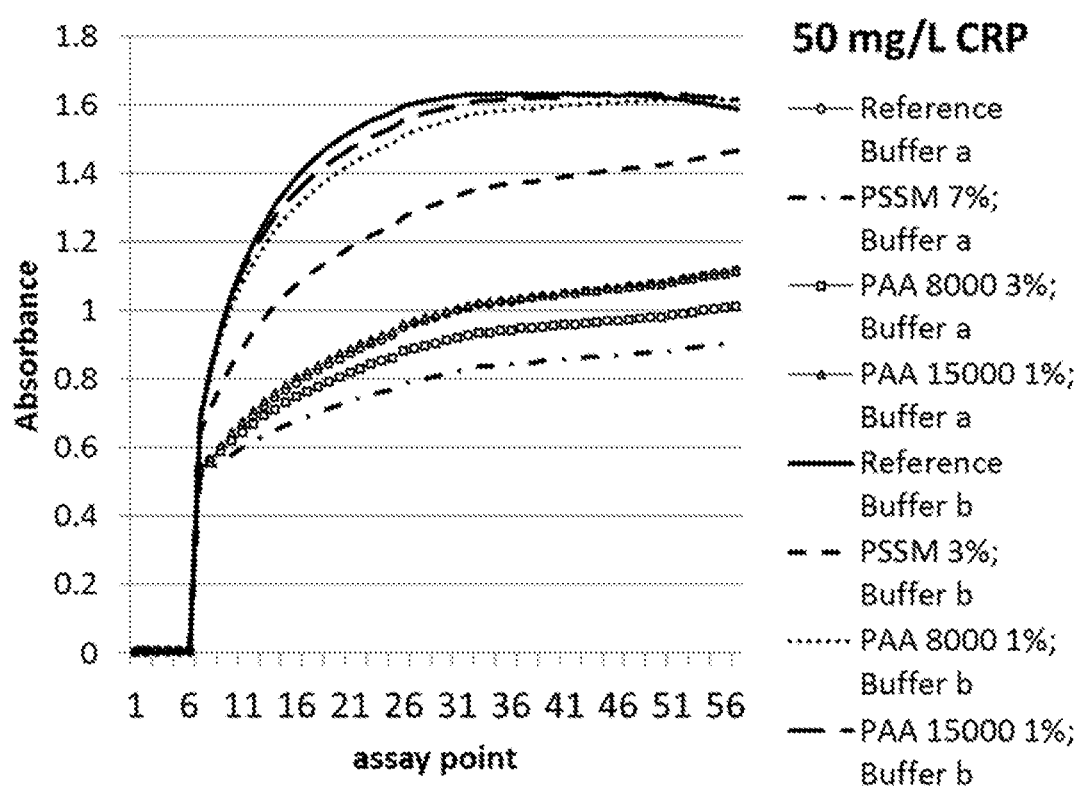
FIG. 5C: Modulator compounds as CRP-assay dual modulators: change of absorbance of a homogenous CRP assay over time in a control assay or in the presence of 300 mg/L CRP as modulator.

PSSM was assessed in concentrations of 1%, 3%, 5% and 7% in both buffer formulations R1a and R1b. For the R1a buffer formulation it was found, that the best dual effect, namely the acceleration of the low analyte concentration and the retardation of the mid and high analyte concentration, was found at a PSSM concentration of 7% in and for the R1b buffer at 3%, whereas the best dual modulation was achieved with R1a (179% signal intensity for low CRP concentration and 32% signal intensity for high CRP concentration in comparison with the reference buffer with 100% signal intensity). PAA (8 kDa) was used in concentrations of 1%, 3%, 5% and 7% in both buffer formulations R1a and R1b. The best effect in R1a was found at 3% PAA and at 1% PAA for buffer R1b. PAA (8 kDa) was used in concentrations of 1%, 3%, 5% and 7% in both buffer formulations R1a and R1b. For both buffers R1a and R1b 1% PAA yielded the best dual modulating effect. The kinetic curves of selected compound concentrations for each of the buffers are depicted in FIG. 5.

TABLE 9

Conditions for assessment of compounds as CRP dual modulators (buffer R1a)

| | |
|---|---|
| Pipetting | 2 μL sample and 150 μL assay buffer (R1) are added subsequently to the reaction cell, followed by the addition of 48 μL of the latex reagent (R2), diluted with 24 μl diluent (water) |
| Assay type | Two-point-end |
| Wavelength (main/sub) | 570 nm/800 nm |
| Calibrators/ calibration mode | 6 calibrators/6-point spline |

TABLE 9-continued

Conditions for assessment of compounds as CRP dual modulators (buffer R1a)

| | |
|---|---|
| Measuring range | 0.3-350 mg/L |
| Samples | Human serum, spiked with human CRP at concentrations covering the measuring range:<br>Analyte-free = 0 mg/L,<br>Low = 5 mg/L, Mid = 50 mg/L and high = 300 mg/L |
| Reaction time/assay points | 10 min/8-18 |
| R2 reagent | Latex particles coated with anti-CRP from mouse in glycine buffer 50 mmol/L, pH 8.0, immunoglobulins from mouse 0.01% and preservatives |
| R1a reagent variations | TRIS buffer 50 mmol/L, pH 7.4, with bovine serum albumin 0.15%, calcium chloride hydrate 0.2%, 1.6% sodium bromide, choline chloride 20% and preservatives<br>(reference buffer)<br>TRIS buffer 50 mmol/L, pH 7.4, with bovine serum albumin 0.15%, calcium chloride hydrate 0.2%, 1.6% sodium bromide, choline chloride 20% and preservatives<br>+1.0%, 3.0%, 5.0% or 7.0% PSSM<br>TRIS buffer 50 mmol/L, pH 7.4, with bovine serum albumin 0.15%, calcium chloride hydrate 0.2%, 1.6% sodium bromide, choline chloride 20% and preservatives<br>+1.0%, 3.0%, 5.0% or 7.0% PAA (8.000 Da)<br>TRIS buffer 50 mmol/L, pH 7.4, with bovine serum albumin 0.15%, calcium chloride hydrate 0.2%, 1.6% sodium bromide, choline chloride 20% and preservatives<br>+1.0%, 3.0%, 5.0% or 7.0% PAA (15.000 Da) |

TABLE 10

Conditions for assessment of compounds as CRP dual modulators (buffer R1b)

| | |
|---|---|
| Pipetting | 21 μL sample and 150 μL assay buffer (R1) are added subsequently to the reaction cell, followed by the addition of 48 μL off the latex reagent (R2), diluted with 24 μl diluent (water) |
| Assay type | Two-point-end |
| Wavelength (main/sub) | 570 nm/800 nm |
| Calibrators/calibration mode | 6 calibrators/6-point spline |
| Measuring range | 0.3-350 mg/L |
| Samples | Human serum, spiked with human CRP at concentrations covering the measuring range:<br>Analyte-free = 0 mg/L,<br>Low = 5 mg/L, Mid = 50 mg/L and high = 300 mg/L |
| Reaction time/assay points | 10 min/7-10 |
| R2 reagent | Latex particles coated with anti-CRP from mouse in glycine buffer 50 mmol/L, pH 8.0, immunoglobulins from mouse 0.01% and preservatives |
| R1b reagent variations | TRIS buffer 50 mmol/L, pH 7.4, with bovine serum albumin 0.15%, calcium chloride hydrate 0.2%, 0.5% PVA, 0.5% Tween 20 and preservatives (reference buffer)<br>TRIS buffer 50 mmol/L, pH 7.4, with bovine serum albumin 0.15%, calcium chloride hydrate 0.2%, 0.5% PVA, 0.5% Tween 20 and preservatives<br>+1.0%, 3.0%, 5.0% or 7.0% PSSM<br>TRIS buffer 50 mmol/L, pH 7.4, with bovine serum albumin 0.15%, calcium chloride hydrate 0.2%, 0.5% PVA, 0.5% Tween 20 and preservatives<br>+1.0%, 3.0%, 5.0% or 7.0% PAA (8.000 Da)<br>TRIS buffer 50 mmol/L, pH 7.4, with bovine serum albumin 0.15%, calcium chloride hydrate 0.2%, 0.5% PVA, 0.5% Tween 20 and preservatives<br>+1.0%, 3.0%, 5.0% or 7.0% PAA (15.000 Da) |

TABLE 11

Modulator compounds as CRP-assay dual modulators

| Buffer R1a | Ref. without | 1.00% | 3% | 5.0% | 7.0% |
|---|---|---|---|---|---|
| CRP in mg/L | | PSSM in % | | | |
| CRP in mg/L | | Abs (570-800 nm; assay points 18-8) | | | |
| 5 | 0.0484 | n.a. | 0.063 | 0.074 | 0.087 |
| 50 | 0.260 | | 0.178 | 0.168 | 0.163 |
| 300 | 0.550 | | 0.204 | 0.179 | 0.173 |
| CRP in mg/L | | percentage of absorbance relative to the reference | | | |
| 5 | 100% | n.a. | 130% | 152% | 179% |
| 50 | 100% | | 68% | 65% | 63% |
| 300 | 100% | | 37% | 33% | 32% |

| | Polyacrylic acid 8000 Da | | | | |
|---|---|---|---|---|---|
| | Ref. without | 1% | 3% | 5% | 7% |
| CRP in mg/L | | Abs (570-800 nm; assay points 18-8) | | | |
| 5 | 0.047 | 0.076 | 0.116 | n.a. | n.a. |
| 50 | 0.257 | 0.256 | 0.221 | | |
| 300 | 0.555 | 0.468 | 0.306 | | |
| CRP in mg/L | | percentage of absorbance relative to the reference | | | |
| 5 | 100% | 161% | 246% | n.a. | n.a. |
| 50 | 100% | 99% | 86% | | |
| 300 | 100% | 84% | 55% | | |

| | Polyacrylic acid 15000 Da | | | | |
|---|---|---|---|---|---|
| | Ref. without | 1% | 3% | 5% | 7% |
| CRP in mg/L | | Abs (570-800 nm; assay points 18-8) | | | |
| 5 | 0.0472 | 0.0762 | n.a. | n.a. | n.a. |
| 50 | 0.2572 | 0.2729 | | | |
| 300 | 0.555 | 0.5176 | | | |
| CRP in mg/L | | percentage of absorbance relative to the reference | | | |
| 5 | 100% | 161% | n.a. | n.a. | n.a. |
| 50 | 100% | 106% | | | |
| 300 | 100% | 93% | | | |

| Buffer R1b | Ref. without | 1.00% | 3% | 5.0% | 7.0% |
|---|---|---|---|---|---|
| | | PSSM in % | | | |
| CRP in mg/L | | Abs (570-800 nm; assay points 10-7) | | | |
| 5 | 0.0556 | 0.0625 | 0.062 | n.a. | n.a. |
| 50 | 0.370 | 0.2709 | 0.196 | | |
| 300 | 0.725 | 0.5875 | 0.293 | | |
| CRP in mg/L | | percentage of absorbance relative to the reference | | | |
| 5 | 100% | 112% | 112% | n.a. | n.a. |
| 50 | 100% | 73% | 53% | | |
| 500 | 100% | 81% | 40% | | |

| | Polyacrylic acid 8000 Da | | | | |
|---|---|---|---|---|---|
| | Ref. without | 1% | 3% | 5% | 7% |
| CRP in mg/L | | Abs (570-800 nm; assay points 18-8) | | | |
| 5 | 0.057 | 0.0972 | n.a. | n.a. | n.a. |
| 50 | 0.368 | 0.337 | | | |
| 300 | 0.7234 | 0.612 | | | |

TABLE 11-continued

Modulator compounds as CRP-assay dual modulators

| CRP in mg/L | | percentage of absorbance relative to the reference | | | |
|---|---|---|---|---|---|
| 5 | 100% | 170% | n.a. | n.a. | n.a. |
| 50 | 100% | 92% | | | |
| 300 | 100% | 85% | | | |

| | Polyacrylic acid 15000 Da | | | | |
|---|---|---|---|---|---|
| | Ref. without | 1% | 3% | 5% | 7% |
| CRP in mg/L | | Abs (570-800 nm; assay points 18-8) | | | |
| 5 | 0.0572 | 0.1005 | n.a. | n.a. | n.a. |
| 50 | 0.3682 | 0.3594 | | | |
| 300 | 0.7234 | 0.6358 | | | |
| CRP in mg/L | | percentage of absorbance relative to the reference | | | |
| 5 | 100% | 176% | n.a. | n.a. | n.a. |
| 50 | 100% | 98% | | | |
| 300 | 100% | 88% | | | |

Example 7. Properties of Selected Modulating Compounds

Selected modulating compounds were analyzed with respect to their physical properties. Their viscosity, density, surface tension and absorption at 340 to 800 nm were measured at room temperature using commercially available, state-of-the-art equipment. The results are shown in the Tables 12-17. The measured viscosity, surface tension and density of the modulators found in the chapters 2 to 6 are within the range that is compatible with the pipetting specs of lab analyzers. Also the densities found for the modulating solutions for the CRP assay are compatible for latex-enhanced tests (density of latex particles: 1.05 g/cm3). The absorption properties are also compatible with the working range of the analyzer which is between 340 and 800 nm; in this wavelength region the compounds do not show an appreciable absorption which could lead to a noticeable offset of the photometric assay signal depending on the wavelength at which an assay is measured. The modulating compounds depicted in the Tables 12-17 are also soluble at temperatures below room temperature: for this purpose, the modulator containing solutions were store at 4° C. for 2 days and afterwards analyzed by eye and photometric means, ensuring that there is neither turbidity nor sedimented material formed. This solubility at lower temperatures allows to store the test kits on-board of the clinical chemistry analyzers, which usually have an on-board refrigeration. The on-board refrigeration prevents reagent evaporation and degradation, ensuring long-term on-board stability and long calibration intervals.

TABLE 12

Physical properties of enhancers of CRP assay (buffer: TRIS buffer 50 mmol/L, pH 7.4, with bovine serum albumin 0.15%, calcium chloride hydrate 0.2%, 1.6% sodium bromide, choline chloride 20%, preservatives)

| Modulator and concentration | Viscosity [mPa * s] | Surface tension [mN/m] | Density [g/cm$^3$] | UV/Vis absorption @ 340-800 nm |
|---|---|---|---|---|
| PAMPS, 0.75% | 4.4 | 50.4 | 1.054 | No |
| Aminodextran, 2.5% | 5.0 | 50.3 | 1.061 | No |
| Carboxymethyldextran, 1.5% | 3.7 | 49.5 | 1.057 | No |

TABLE 13

Physical properties of inhibitors of CRP assay (buffer: TRIS buffer 50 mmol/L, pH 7.4, with bovine serum albumin 0.15%, calcium chloride hydrate 0.2%, 0.5% PVA, 0.5% Tween 20, preservatives)

| Modulator and concentration | Viscosity [mPa * s] | Surface tension [mN/m] | Density [g/cm$^3$] | UV/Vis absorption @ 340-800 nm |
|---|---|---|---|---|
| Triethanolamine, 1.5M | 2.5 | 35.8 | 1.020 | No |
| Triethylamine, 1.5M | 2.1 | 39.3 | 1.009 | No |

TABLE 14

Physical properties of enhancer of Albumin assay (buffer: TRIS buffer 50 mmol/L, pH 8.0, Tween 20 1%, EDTA 2.0 mmol/L, preservatives)

| Modulator and concentration | Viscosity [mPa * s] | Surface tension [mN/m] | Density [g/cm$^3$] | UV/Vis absorption @ 340-800 nm |
|---|---|---|---|---|
| Carboxymethyldextran, 2.5% | 6.7 | 39.2 | 1.013 | No |

TABLE 15

Physical properties of inhibitors of Albumin assay (buffer: TRIS buffer 50 mmol/L, pH 8.0, Tween 20 1%, PEG 4%, preservatives)

| Modulator and concentration | Viscosity [mPa * s] | Surface tension [mN/m] | Density [g/cm$^3$] | UV/Vis absorption @ 340-800 nm |
|---|---|---|---|---|
| Triethanolamine, 1M | 3.3 | 37.9 | 1.041 | No |
| Taurine, 3% | 2.2 | 38.5 | 1.022 | No |
| PAMPS, 1% | 8.8 | 40.8 | 1.013 | No |
| Aminodextran, 4% | 8.1 | 41.2 | 1.024 | No |

TABLE 16

Physical properties of dual modulators of CRP assay in buffer R1a (TRIS buffer 50 mmol/L, pH 7.4, with bovine serum albumin 0.15%, calcium chloride hydrate 0.2%, 1.6% sodium bromide, choline chloride 20%, preservatives)

| Modulator and concentration | Viscosity [mPa * s] | Surface tension [mN/m] | Density [g/cm$^3$] | UV/Vis absorption @ 340-800 nm |
|---|---|---|---|---|
| PAA (8.000 Da), 3% | 2.5 | 48.5 | 1.070 | No |
| PSSM, 7% | 3.6 | 47.7 | 1.086 | No |

TABLE 17

Physical properties of dual modulators of CRP assay in buffer R1b (TRIS buffer 50 mmol/L, pH 7.4, with bovine serum albumin 0.15%, calcium chloride hydrate 0.2%, 0.5% PVA, 0.5% Tween 20, preservatives)

| Modulator and concentration | Viscosity [mPa * s] | Surface tension [mN/m] | Density [g/cm$^3$] | UV/Vis absorption @ 340-800 nm |
|---|---|---|---|---|
| PAA (8.000 Da), 1% | 1.4 | 39.8 | 1.050 | No |
| PSSM, 3% | 1.8 | 38.6 | 1.070 | No |

The invention claimed is:

1. A method for determining an analyte in a sample in an interaction assay, said method comprising contacting said sample with 0.75% to 5.25% of an interaction modulator in said interaction assay and detecting an optical signal that correlates to a concentration of said analyte, wherein said interaction modulator is an enhancer of said interaction assay at low analyte concentrations and is a retarder of said interaction assay at high analyte concentrations and wherein said interaction modulator is a copolymer of 4-styrenesulfonic acid and maleic acid PSSM) or Polyacrylic acid (PAA), wherein said interaction assay is a homogenous agglutination immunoassay, wherein said analyte is a C-reactive protein (CRP).

2. The method of claim 1, wherein said PSSM has a repeating structural unit according to formula (I):

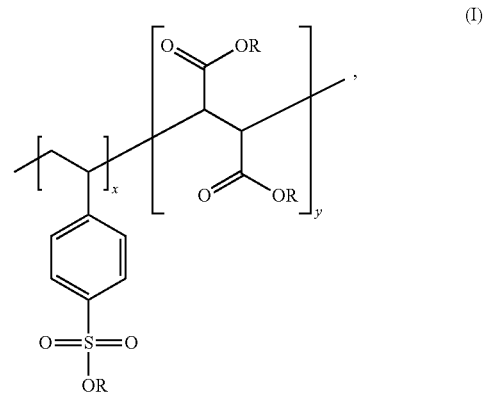

with x and y being integers selected from 1, 2, 3, 4, and 5, said selection being independent for x and y and for each repeating unit; and R being H or a cation; and wherein said PSSM has a molecular weight of from 1 kDa to 100 kDa.

3. The method of claim 1, wherein said PSSM has a molecular weight of from 5 kDa to 50 kDa.

4. The method of claim 1, wherein said PAA has a repeating structural unit according to formula (II):

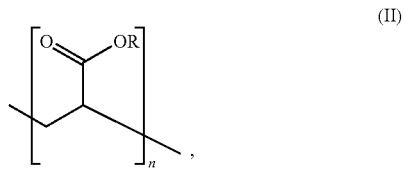

with R being H or a cation; and wherein said PAA has a molecular weight of from 1 kDa to 50 kDa.

5. The method of claim 1, wherein said interaction assay is a bead-enhanced agglutination immunoassay.

6. The method of claim 1, wherein said interaction assay comprises photo-optical detection.

7. A method for determining an analyte in a sample in an interaction assay, said method comprising contacting said sample with an interaction modulator in said interaction assay and detecting an optical signal that correlates to a concentration of said analyte, wherein said interaction modulator is selected from the group consisting of 0.75% to 7% PSSM, 0.5% to 4% aminodextran, 0.5% to 2.5% carboxymethyldextran, 0.25% to 1% Poly-(2-acrylamido-2-methyl-1-propanesulfonic acid (PAMPS), 0.05 M to 1 M triethylamine, 0.05 M to 1 M triethanolamine, 0.5% to 3% taurine, and 1% to 3% dodecylsulfate, wherein said interaction assay is a homogenous agglutination immunoassay, wherein said analyte is a C-reactive protein (CRP) or albumin, and wherein said PAMPS has a repeating structural unit according to formula (III):

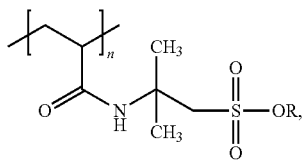

(III)

with R being H or a cation, and wherein said PAMPS has a molecular weight of from 100 kDa to 10000 kDa.

8. The method of claim 7, wherein said PSSM has a repeating structural unit according to formula (I):

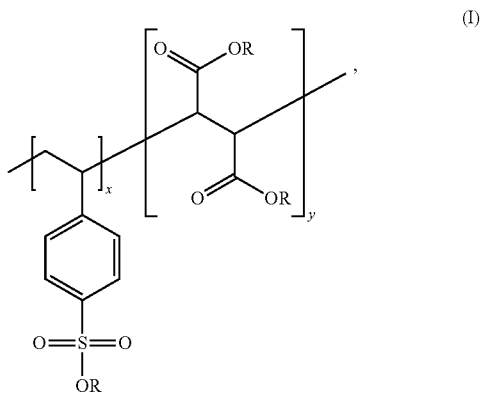

(I)

with x and y being integers selected from 1, 2, 3, 4, and 5, said selection being independent for x and y and for each repeating unit;

R being H or a cation, and wherein said PSSM has a molecular weight of from 1 kDa to 100 kDa.

9. The method of claim 7, wherein said interaction modulator comprises a sulfonylated compound.

10. The method of claim 7, wherein said interaction assay comprises photo-optical detection.

* * * * *